(12) United States Patent
Srinivisan et al.

(10) Patent No.: US 6,271,354 B1
(45) Date of Patent: Aug. 7, 2001

(54) CHIMERIC VIRAL PROTEINS

(75) Inventors: Alagarsamy Srinivisan, Glen Mills; Hilary Koprowski, Wynnewood, both of PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/053,941

(22) Filed: Apr. 2, 1998

Related U.S. Application Data

(60) Provisional application No. 60/043,380, filed on Apr. 3, 1997.

(51) Int. Cl.[7] .......................... C12P 21/08; C07K 16/00; A01N 65/00; A61K 39/385; A61K 39/21
(52) U.S. Cl. .................. 530/387.3; 530/388.26; 530/388.35; 424/192.1; 424/196.4; 424/208.1; 424/230.1; 424/231.1
(58) Field of Search ..................... 424/192.1, 196.11, 424/208.1, 230.1, 231.1; 530/387.3, 388.26, 388.35

(56) References Cited

U.S. PATENT DOCUMENTS

| | | | |
|---|---|---|---|
| 5,142,025 | 8/1992 | Putney et al. | 530/350 |
| 5,310,876 | 5/1994 | Bayer et al. | 530/350 |
| 5,439,809 | 8/1995 | Haynes et al. | 435/69.3 |
| 5,443,828 | 8/1995 | Kang et al. | 424/188.1 |
| 5,576,421 | 11/1996 | Saito et al. | 530/350 |
| 5,580,773 | 12/1996 | Kang et al. | 435/236 |

OTHER PUBLICATIONS

D. Serio et al. "Developement of a novel anit–HIV–1 agent from within: Effect of chimeric Vpr–containing protease cleavage site residues on virus replication". Proc. Natl. Acad. Sci. USA vol. 94, pp. 3346–3351, Apr. 1997 Microbiology.
PCT International Search Report for International Application PCT/US98/06463.

*Primary Examiner*—Hankyel T. Park
(74) *Attorney, Agent, or Firm*—ReedSmith LLP; William J. McNichol; Nanda P. B. A. Kun

(57) ABSTRACT

Chimeric viral proteins and nucleic acid constructs that code for them and are useful as therapeutic agents.

18 Claims, 12 Drawing Sheets

| | Cleavage site Sequences | Vpr 3' end |
|---|---|---|
| Vpr 17-24 | CCCCCCTCGAGCTAGTTCTGCACTATAGGGTAATTTTGGCTGACGGATCTACTGGCTCCATT | |
| Vpr 24/2 | CCCCCCTCGAGCTAGCTCATTGCTTCAGCCAAAACTCTTGCTTTGGATCTACTGGCTCCATT | |
| Vpr 2/7 | CCCCCCTCGAGCTAATTGCCTTTCTGTATCATTATGGTAGCTGGGGATCTACTGGCTCCATT | |
| Vpr 7/1 | CCCCCCTCGAGCTAGATCTTCCCTAAAAAATTAGCCTGTCTCTCGGATCTACTGGCTCCATT | |
| Vpr 1/6 | CCCCCCTCGAGCTATGGTCTGCTCTGAAGAAAATTCCCTGGCCTGGATCTACTGGCTCCATT | |
| Vpr TF/PR | CCCCCCTCGAGCTAAAGAGTGATCTGAGGCAAGCTAAAGGATACGGATCTACTGGCTCCATT | |
| Vpr PR/RT | CCCCCCTCGAGCTAAATAGGACTAATGGGAAAATTTAAAGTGCAGGATCTACTGGCTCCATT | |
| Vpr RT/RNaseH | CCCCCCTCGAGCTATGCCCCATCTACATAGAAAGTTTCTGCTCCGGATCTACTGGCTCCATT | |
| Vpr RT/IN | CCCCCCTCGAGCTATATTCCATCTAAAAATAGTACTTTCCTGATGGATCTACTGGCTCCATT | |
| Vpr F | CCCCCCTCGAGCTACTTGTCATCGTCGTCCTTGTAGTCGGATCTACTGGCTCCATT | |

FIG. 1

| | Cleavage site Sequences | Vpr 3' end |
|---|---|---|
| Vpr 17-24 | CCCCCCTCGAGCTAGTTCTGCACTATAGGGTAATTTGGCTGACGGATCTACTGGCTCCATT | |
| Vpr 24/2 | CCCCCCTCGAGCTAGCTAGCTCATTGCTTCAGCCAAAACTCTTGCTTGATCTACTGGCTCCATT | |
| Vpr 2/7 | CCCCCCTCGAGCTAATTGCCTTTCTGTATCATTATGGTAGCTACTACTGGCTCCATT | |
| Vpr 7/1 | CCCCCCTCGAGCTAGATCTTCCCTAAAAAATTAGCCTGTCTCTCGGATCTACTGGCTCCATT | |
| Vpr 1/6 | CCCCCCTCGAGCTATGGTCTGTCTGAAGAAAATTCCCTGGCCTGGATCTACTGGCTCCATT | |
| Vpr TF/PR | CCCCCCTCGAGCTAAAGAGTGATCTGAGGCAAGCTAAAGGATACGGATCTACTGGCTCCATT | |
| Vpr PR/RT | CCCCCCTCGAGCTAAATAGGACTAATGGGAAAATTTAAAGTGCAGGATCTACTGGCTCCATT | |
| Vpr RT/RNaseH | CCCCCCTCGAGCTATGCCCCATCTACATAGAAAGTTTCTGCTCCGATCTACTGGCTCCATT | |
| Vpr RT/IN | CCCCCCTCGAGCTATATTCCATCTAAAAATAGTACTTCCTGATGGATCTACTGGCTCCATT | |
| Vpr F | CCCCCCTCGAGCTACTGTCATGTCGTCCTTGTAGTCGGATCTACTGGCTCCATT | |

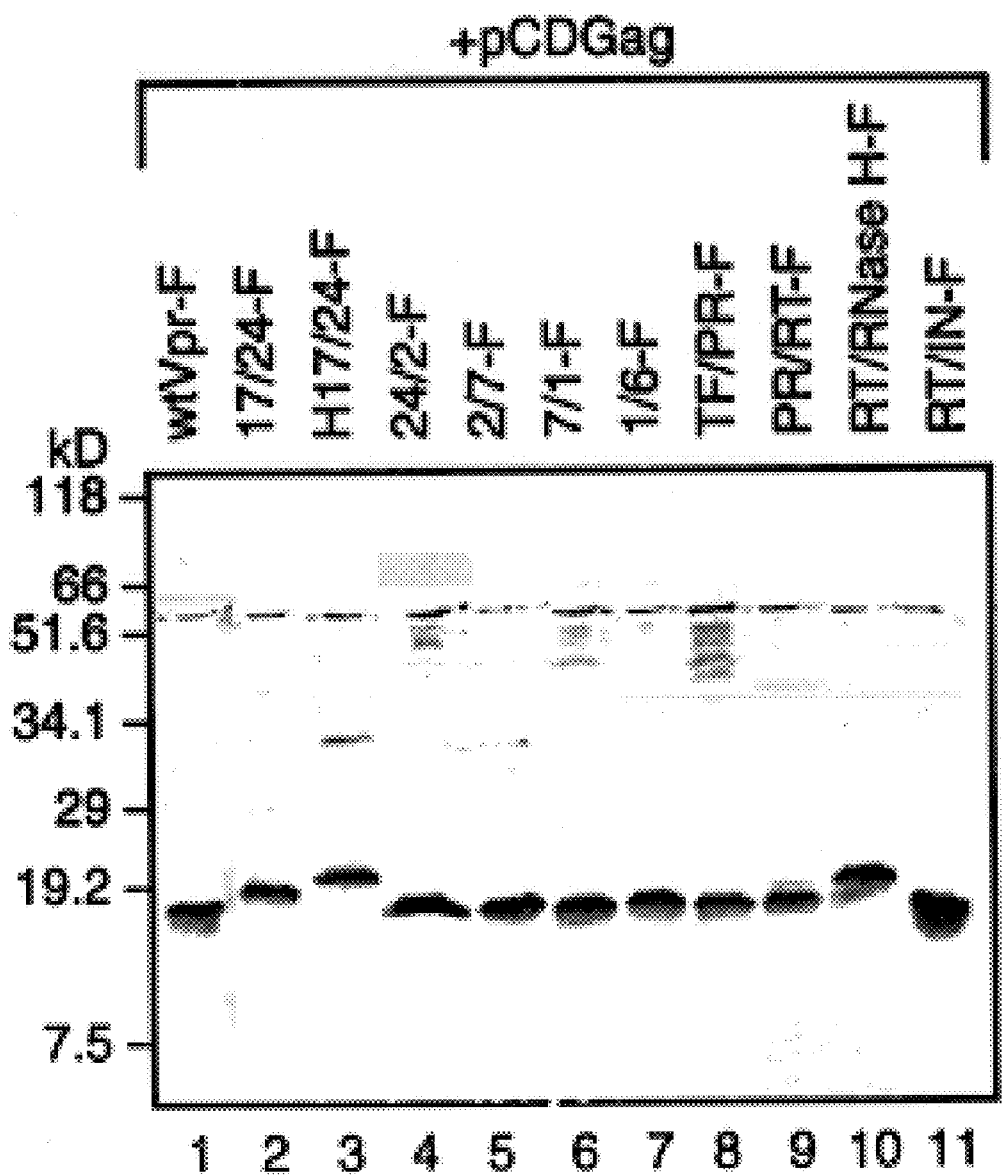

FIG. 5
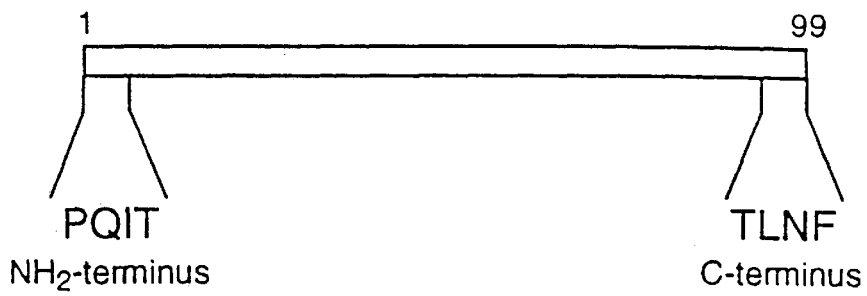
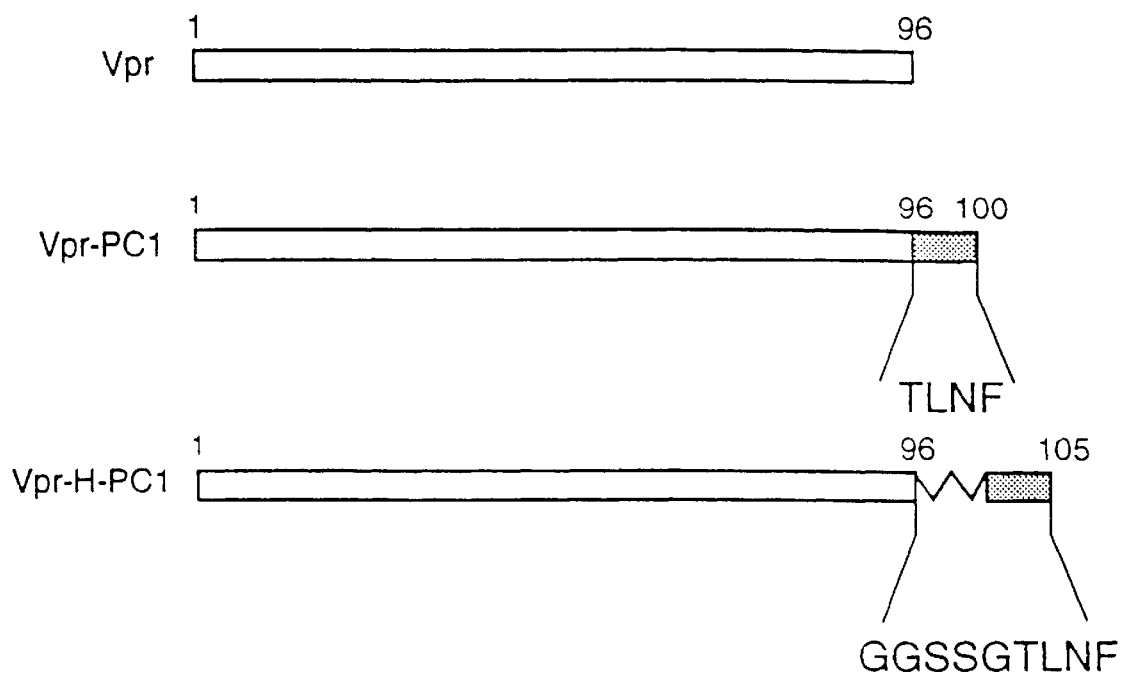

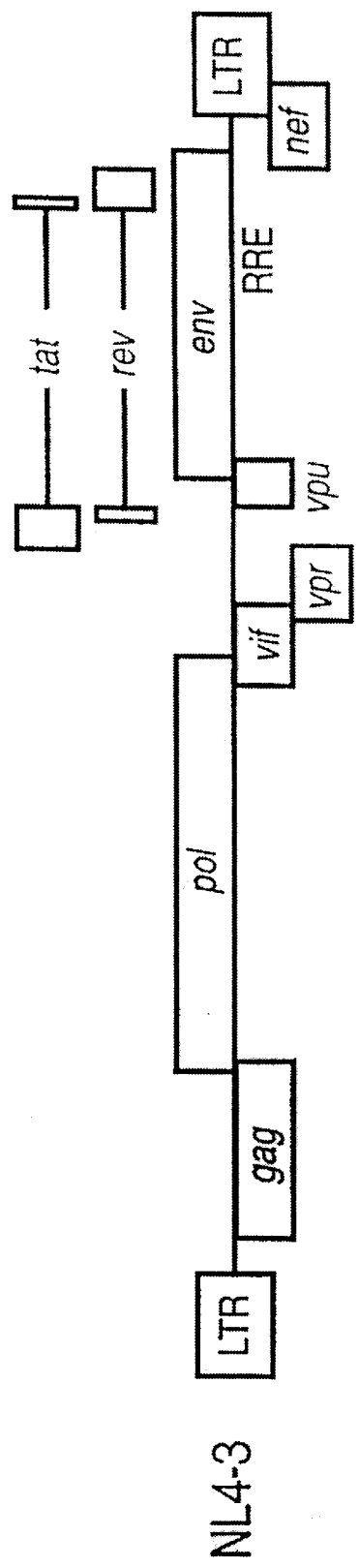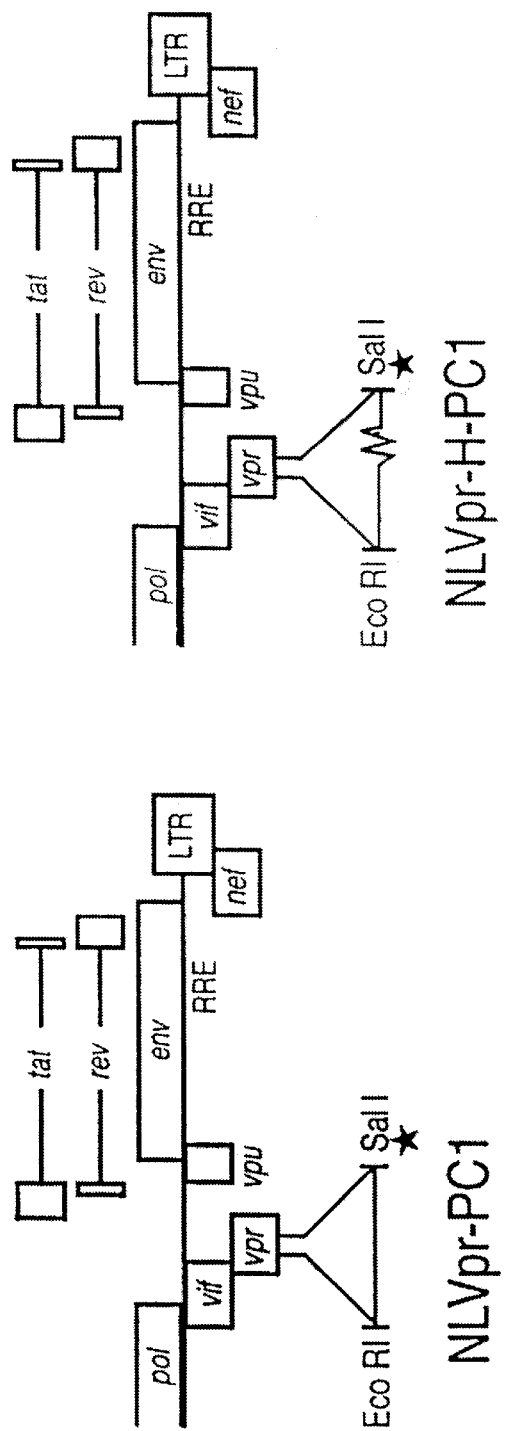
FIG. 8A

SEQUENCE LISTING

```
<160> NUMBER OF SEQ ID NOS: 25

<210> SEQ ID NO: 1
<211> LENGTH: 8
<212> TYPE: PRT
<213> ORGANISM: Artificial Sequence
<220> FEATURE:
<223> OTHER INFORMATION: Description of Artificial Sequence:  FLAG
      epitope

<400> SEQUENCE: 1

Asp Tyr Lys Asp Asp Asp Asp Lys
  1               5

<210> SEQ ID NO: 2
<211> LENGTH: 5
<212> TYPE: PRT
<213> ORGANISM: Artificial Sequence
<220> FEATURE:
<223> OTHER INFORMATION: Description of Artificial Sequence: hinge
      region

<400> SEQUENCE: 2

Gly Gly Ser Ser Gly
  1               5

<210> SEQ ID NO: 3
<211> LENGTH: 5
<212> TYPE: PRT
<213> ORGANISM: Artificial Sequence
```

```
<220> FEATURE:
<223> OTHER INFORMATION: Description of Artificial Sequence: protein
      kinase domain

<400> SEQUENCE: 3

Arg Arg Ala Ser Val
  1               5

<210> SEQ ID NO: 4
<211> LENGTH: 62
<212> TYPE: DNA
<213> ORGANISM: Artificial Sequence
<220> FEATURE:
<223> OTHER INFORMATION: Description of Artificial Sequence: chimera of
      Vpr and cleavage site DNA sequences
<300> PUBLICATION INFORMATION:
<303> JOURNAL: Meth. Enzymol.
<304> VOLUME: 38
<306> PAGES: 299-
<307> DATE: 1974

<400> SEQUENCE: 4
cccccctcga gctagttctg cactataggg taatttttggc tgacggatct actggctcca      60
tt                                                                     62

<210> SEQ ID NO: 5
<211> LENGTH: 62
<212> TYPE: DNA
<213> ORGANISM: Artificial Sequence
<220> FEATURE:
<223> OTHER INFORMATION: Description of Artificial Sequence: chimera of
      Vpr and cleavage site DNA sequences
<300> PUBLICATION INFORMATION:
<303> JOURNAL: Meth. Enzymol.
<304> VOLUME: 38
<306> PAGES: 299-
<307> DATE: 1974

<400> SEQUENCE: 5
cccccctcga gctagctcat tgcttcagcc aaaactcttg ctttggatct actggctcca      60
tt                                                                     62

<210> SEQ ID NO: 6
<211> LENGTH: 62
<212> TYPE: DNA
<213> ORGANISM: Artificial Sequence
<220> FEATURE:
<223> OTHER INFORMATION: Description of Artificial Sequence: chimera of
      Vpr and cleavage site DNA sequences
<300> PUBLICATION INFORMATION:
<303> JOURNAL: Meth. Enzymol.
<304> VOLUME: 38
<306> PAGES: 299-
<307> DATE: 1974

<400> SEQUENCE: 6
cccccctcga gctaattgcc tttctgtatc attatggtag ctggggatct actggctcca      60
tt                                                                     62

<210> SEQ ID NO: 7
<211> LENGTH: 62
<212> TYPE: DNA
<213> ORGANISM: Artificial Sequence
<220> FEATURE:
<223> OTHER INFORMATION: Description of Artificial Sequence: chimera of
      Vpr and cleavage site DNA sequences
<300> PUBLICATION INFORMATION:
<303> JOURNAL: Meth. Enzymol.
```

```
<304> VOLUME: 38
<306> PAGES: 299-
<307> DATE: 1974

<400> SEQUENCE: 7
cccccctcga gctagatctt ccctaaaaaa ttagcctgtc tctcggatct actggctcca      60
tt                                                                     62

<210> SEQ ID NO: 8
<211> LENGTH: 62
<212> TYPE: DNA
<213> ORGANISM: Artificial Sequence
<220> FEATURE:
<223> OTHER INFORMATION: Description of Artificial Sequence: chimera of
      Vpr and cleavage site DNA sequences
<300> PUBLICATION INFORMATION:
<303> JOURNAL: Meth. Enzymol.
<304> VOLUME: 38
<306> PAGES: 299-
<307> DATE: 1974

<400> SEQUENCE: 8
cccccctcga gctatggtct gctctgaaga aaattccctg gcctggatct actggctcca      60
tt                                                                     62

<210> SEQ ID NO: 9
<211> LENGTH: 62
<212> TYPE: DNA
<213> ORGANISM: Artificial Sequence
<220> FEATURE:
<223> OTHER INFORMATION: Description of Artificial Sequence: chimera of
      Vpr and cleavage site DNA sequences
<300> PUBLICATION INFORMATION:
<303> JOURNAL: Meth. Enzymol.
<304> VOLUME: 38
<306> PAGES: 299-
<307> DATE: 1974

<400> SEQUENCE: 9
cccccctcga gctaaagagt gatctgaggc aagctaaagg atacggatct actggctcca      60
tt                                                                     62

<210> SEQ ID NO: 10
<211> LENGTH: 62
<212> TYPE: DNA
<213> ORGANISM: Artificial Sequence
<220> FEATURE:
<223> OTHER INFORMATION: Description of Artificial Sequence: chimera of
      Vpr and cleavage site DNA sequences
<300> PUBLICATION INFORMATION:
<303> JOURNAL: Meth. Enzymol.
<304> VOLUME: 38
<306> PAGES: 299-
<307> DATE: 1974

<400> SEQUENCE: 10
cccccctcga gctaaatagg actaatggga aaatttaaag tgcaggatct actggctcca      60
tt                                                                     62

<210> SEQ ID NO: 11
<211> LENGTH: 62
<212> TYPE: DNA
<213> ORGANISM: Artificial Sequence
<220> FEATURE:
<223> OTHER INFORMATION: Description of Artificial Sequence: chimera of
      Vpr and cleavage site DNA sequences
<300> PUBLICATION INFORMATION:
```

```
<303> JOURNAL: Meth. Enzymol.
<304> VOLUME: 38
<306> PAGES: 299-
<307> DATE: 1974

<400> SEQUENCE: 11
cccccctcga gctatgcccc atctacatag aaagtttctg ctccggatct actggctcca      60
tt                                                                     62

<210> SEQ ID NO: 12
<211> LENGTH: 62
<212> TYPE: DNA
<213> ORGANISM: Artificial Sequence
<220> FEATURE:
<223> OTHER INFORMATION: Description of Artificial Sequence: chimera of
      Vpr and cleavage site DNA sequences
<300> PUBLICATION INFORMATION:
<303> JOURNAL: Meth. Enzymol.
<304> VOLUME: 38
<306> PAGES: 299-
<307> DATE: 1974

<400> SEQUENCE: 12
cccccctcga gctatattcc atctaaaaat agtactttcc tgatggatct actggctcca      60
tt                                                                     62

<210> SEQ ID NO: 13
<211> LENGTH: 56
<212> TYPE: DNA
<213> ORGANISM: Artificial Sequence
<220> FEATURE:
<223> OTHER INFORMATION: Description of Artificial Sequence:  chimera of
      Vpr and FLAG sequences
<300> PUBLICATION INFORMATION:
<303> JOURNAL: Meth. Enzymol.
<304> VOLUME: 38
<306> PAGES: 299-
<307> DATE: 1974

<400> SEQUENCE: 13
cccccctcga gctacttgtc atcgtcgtcc ttgtagtcgg atctactggc tccatt          56

<210> SEQ ID NO: 14
<211> LENGTH: 10
<212> TYPE: PRT
<213> ORGANISM: Human immunodeficiency virus type 1
<300> PUBLICATION INFORMATION:
<303> JOURNAL: Meth. Enzymol.
<304> VOLUME: 38
<306> PAGES: 299-
<307> DATE: 1974

<400> SEQUENCE: 14

Val Ser Gln Asn Tyr Pro Ile Val Gln Asn
 1               5                  10

<210> SEQ ID NO: 15
<211> LENGTH: 10
<212> TYPE: PRT
<213> ORGANISM: Human immunodeficiency virus type 1
<300> PUBLICATION INFORMATION:
<303> JOURNAL: Meth. Enzymol.
<304> VOLUME: 38
<306> PAGES: 299-
<307> DATE: 1974

<400> SEQUENCE: 15

Lys Ala Arg Val Leu Ala Glu Ala Met Ser
```

```
                1               5                   10

<210> SEQ ID NO: 16
<211> LENGTH: 10
<212> TYPE: PRT
<213> ORGANISM: Human immunodeficiency virus type 1
<300> PUBLICATION INFORMATION:
<303> JOURNAL: Meth. Enzymol.
<304> VOLUME: 38
<306> PAGES: 299-
<307> DATE: 1974

<400> SEQUENCE: 16

Ser Ala Thr Ile Met Met Gln Arg Gly Asn
  1               5                   10

<210> SEQ ID NO: 17
<211> LENGTH: 10
<212> TYPE: PRT
<213> ORGANISM: Human immunodeficiency virus type 1
<300> PUBLICATION INFORMATION:
<303> JOURNAL: Meth. Enzymol.
<304> VOLUME: 38
<306> PAGES: 299-
<307> DATE: 1974

<400> SEQUENCE: 17

Glu Arg Gln Ala Asn Phe Leu Gly Lys Ile
  1               5                   10

<210> SEQ ID NO: 18
<211> LENGTH: 10
<212> TYPE: PRT
<213> ORGANISM: Human immunodeficiency virus type 1
<300> PUBLICATION INFORMATION:
<303> JOURNAL: Meth. Enzymol.
<304> VOLUME: 38
<306> PAGES: 299-
<307> DATE: 1974

<400> SEQUENCE: 18

Arg Pro Gly Asn Phe Leu Gln Ser Arg Pro
  1               5                   10

<210> SEQ ID NO: 19
<211> LENGTH: 10
<212> TYPE: PRT
<213> ORGANISM: Human immunodeficiency virus type 1
<300> PUBLICATION INFORMATION:
<303> JOURNAL: Meth. Enzymol.
<304> VOLUME: 38
<306> PAGES: 299-
<307> DATE: 1974

<400> SEQUENCE: 19

Val Ser Phe Ser Phe Pro Gln Ile Thr Leu
  1               5                   10

<210> SEQ ID NO: 20
<211> LENGTH: 10
<212> TYPE: PRT
<213> ORGANISM: Human immunodeficiency virus type 1
<300> PUBLICATION INFORMATION:
<303> JOURNAL: Meth. Enzymol.
<304> VOLUME: 38
<306> PAGES: 299-
<307> DATE: 1974

<400> SEQUENCE: 20
```

```
Cys Thr Leu Asn Phe Pro Ile Ser Pro Ile
  1               5                  10

<210> SEQ ID NO: 21
<211> LENGTH: 10
<212> TYPE: PRT
<213> ORGANISM: Human immunodeficiency virus type 1
<300> PUBLICATION INFORMATION:
<303> JOURNAL: Meth. Enzymol.
<304> VOLUME: 38
<306> PAGES: 299-
<307> DATE: 1974

<400> SEQUENCE: 21

Gly Ala Glu Thr Phe Tyr Val Asp Gly Ala
  1               5                  10

<210> SEQ ID NO: 22
<211> LENGTH: 10
<212> TYPE: PRT
<213> ORGANISM: Human immunodeficiency virus type 1
<300> PUBLICATION INFORMATION:
<303> JOURNAL: Meth. Enzymol.
<304> VOLUME: 38
<306> PAGES: 299-
<307> DATE: 1974

<400> SEQUENCE: 22

Ile Arg Lys Val Leu Phe Leu Asp Gly Ile
  1               5                  10

<210> SEQ ID NO: 23
<211> LENGTH: 4
<212> TYPE: PRT
<213> ORGANISM: Human immunodeficiency virus type 1

<400> SEQUENCE: 23

Pro Gln Ile Thr
  1

<210> SEQ ID NO: 24
<211> LENGTH: 4
<212> TYPE: PRT
<213> ORGANISM: Human immunodeficiency virus type 1

<400> SEQUENCE: 24

Thr Leu Asn Phe
  1

<210> SEQ ID NO: 25
<211> LENGTH: 9
<212> TYPE: PRT
<213> ORGANISM: Artificial Sequence
<220> FEATURE:
<223> OTHER INFORMATION: Description of Artificial Sequence:  Flag
      protein--HIV-1 protease chimera

<400> SEQUENCE: 25

Gly Gly Ser Ser Gly Thr Leu Asn Phe
  1               5
```

CHIMERIC VIRAL PROTEINS

This application claims the benefit of U.S. Provisional Application No. 60/043,380, filed Apr. 3, 1997, which application is incorporated herein by reference.

This work was supported by funds from the National Institutes of Health (AI29306). It was also supported by a grant from the Commonwealth of Pennsylvania to the Biotechnology Foundation, Inc., and a grant from the Biomedical Research Support Committee and institutional funds.

BACKGROUND

The field of the invention is anti-viral agents.

Effective antiviral agents will be of great value in controlling virus replication and delaying the onset of HIV-1-related disease symptoms. Current therapy involves the use of antiviral agents that target the enzymatic functions of the virus, resulting in the emergence of resistant viruses to these agents, thus lowering effectiveness.

HIV-1 is a member of the lentivirus family of retroviruses. Upon infection with the virus, individuals exhibit a variable onset of AIDS-related diseases (Levy, 1993.). Recent studies have shown that even in the midst of the clinically latent period, there is no virological latency in the infected individuals (Pantaleo et al., 1993; Embretson et al., 1993). Given this scenario, it has been suggested that inhibitors of virus replication will be of immense value in the onset and control of AIDS-related diseases in persons infected with HIV-1 (Ridky et al., 1995; Miller et al., 1996; Mellors et al., 1996; Crowe et al., 1996).

The HIV-1 life cycle shares several features common to all retroviruses. These features include virus attachment to a specific receptor, penetration, uncoating, reverse transcription, translocation of viral DNA from the cytoplasm to the nucleus, integration, expression of viral proteins, assembly, and maturation of virus particles (1). Virally encoded enzymatic activities, which are essential for the processes associated with virus infection, have all been used as targets for developing agents that interfere with the virus replication (2–4). Unfortunately, the use of such antiviral agents has also resulted in the emergence of drug-resistant viruses (5–7). In comparison to the monotherapy, combination therapy involving multiple inhibitors has been shown to be effective (8–11). The emergence of drug-resistant viruses, however, will remain a problem with the continued use of antiviral agents to target viral enzymes. Hence, alternative strategies to contain HIV-1 replication are warranted. Toward this goal, an approach to generate a novel anti-HIV-1 agent from within the virus has been considered.

Unlike the simple retroviruses, the HIV-1 genome contains six auxiliary genes in addition to the gag, pol and env common to all retroviruses. The processes associated with virus infection are carried out by different viral gene products, which makes these proteins potential targets for antiretroviral therapy. These processes include: a) binding to a receptor and virus internalization, b) reverse transcription and transport of viral DNA to the nucleus for integration, c) expression of viral proteins and d) assembly and releases of viral particles from infected cells (Levy, 1993).

Among the auxiliary gene products of HIV-1, vpr, vif, and nef have been shown to be associated with virus particles to a varying extent (12–16). The virion-associated protein Vpr has been an intensive area of interest with respect to understanding the role of Vpr in virus infection. Vpr coding sequences (96 aa) are found to overlap Vif at the 5' end and Tat at the 3' end (17). Characteristic features of Vpr include virion incorporation, cell cycle arrest at the $G_2$ stage, nuclear localization, participation in transport of the preintegration complex, demonstration of cation channel activity, and interaction with several candidate cellular proteins (18–28). Additionally, work from our laboratory and others has shown that Vpr is essential for optimum infection of macrophages (29, 30). Mutational analysis of Vpr has revealed the presence of critical domains needed for its virion incorporation and the importance of the predicted helical domain (amino acids 17–34) in such an event (22, 31–38). The virion specificity and abundance of Vpr in viral particles provide avenues for localizing antiviral agents to progeny virus, giving the ability to interfere with the assembly, maturation, and infectivity of HIV-1.

Upon initial synthesis as a polyprotein precursor, the HIV-1 aspartyl protease has the unique ability to autocatalyze its own cleavage from the Pr160 polyprotein precursor. After its release, the protease is then able to catalyze the cleavage at other sites generating the mature Gag protein, p17, p24, p7, and p6 and the reverse transcriptase (RT) and integrase enzymes. The specific cleavage sites between the proteins in the polyprotein precursor recognized by HIV-1 protease are highly conserved among viral isolates (39).

In the present invention, in order to generate an effective anti-HIV-1 agent from within the virus, we have combined the protease cleavage site residues found in the Gag and Gag-Pol precursor proteins and the virion-specific feature of Vpr. The rationale for this approach is that an inappropriate presentation of chimeric Vpr (Vpr-C) proteins containing protease cleavage signal sequences might interfere with the processing of bona fide viral precursor polyproteins leading to the generation of incompletely processed noninfectious virus particles (2). The differential amount of Gag, Gag-Pol, and Vpr proteins present in the virus particles supports the feasibility of such an approach. The results demonstrate that the above strategy is effective in interfering with HIV-1 virus replication.

As regards a second aspect of the invention, it is relevant that HIV-1 PR is an obligatory homodimer, with the active site made from two monomers containing DTG amino acid residues brought into proximity through regions in the $NH_2$ and COOH termini of the PR monomers, known as the dimer interface (Babé et al., 1991). The dimer interface region of ribonucleotide reductase and DNA polymerase from herpes simplex virus and HIV-1 RT have been investigated as potential targets for developing antiviral agents (Dutia et al., 1986; Cohen et al., 1986; Divita et al., 1994; Digard et al., 1995). It has been suggested that peptides corresponding to the dimer interface structure between the HIV-1 PR subunits may interfere with the generation of an enzymatically active molecule. It is estimated that the C-terminal 4 residues of PR contribute up to 50% of the intersubunit interaction in the dimer (Weber, 1990). A synthetic peptide corresponding to this domain showed dissociative inhibition of HIVI PR in vitro and a weak inhibition of viral replication in cell cultures (Zhang et al., 1991; Schramm et al., 1991; 1993; Babé et al., 1992).

The approach utilized in the second aspect of the invention takes advantage of the dimerization feature of PR and localizes a peptide corresponding to the dimer interface domain (The 4-amino acid sequence, TLNF as represented by the standard single-letter codes for amino acids) in the virus particle through chimeric Vpr. Our concept involves the incorporation of chimeric Vpr into the virus particle along with the Gag and Gag-Pol precursors where it is likely to interfere with the formation of active PR. The lack of availability of active PR will ultimately lead to the generation of immature, non-infectious virus particles due to incomplete processing of viral proteins. The data presented here shows that the presence of chimeric Vpr in viral particles indeed resulted in reduced levels of virus replication.

SUMMARY OF THE INVENTION

In a most general aspect, the invention is a chimeric viral protein comprising:

1) a first protein of a virus; and
2) a polypeptide of said virus, said polypeptide joined by a peptide linkage to said first viral protein in said chimeric protein, said polypeptide not normally joined by said peptide linkage to said polypeptide in said virus or in cells infected by said virus.

In one aspect, the invention is a chimeric viral protein comprising:

1) a first protein of a virus, said first protein not compromising a site for cleavage by a proteolytic enzyme of said virus;
2) a polypeptide proteolytic cleavage site, of said virus, said cleavage site being a site for cleavage by a proteolytic enzyme of said virus;

such that said first protein is covalently linked by a peptide linkage to said polypeptide proteolytic cleavage site.

In a second aspect, the invention is a chimeric viral protein comprising:

1) a first protein of a virus, said first protein not being a protein that forms a dimeric proteolytic enzyme of said virus;
2) a dimer interface polypeptide sequence of an enzyme of said virus, said sequence being one by which monomers of said enzyme combine to form the active dimeric enzyme, such that said first protein is covalently linked by a peptide linkage to said dimer interface polypeptide sequence.

Related aspects of the inventions are nucleic acid constructs that code for the chimeric protein, and the process of administering them as therapeutic agents.

BRIEF DESCRIPTION OF THE DRAWINGS

FIG. 1. Minus strand primers (5'–3') used to generate Vpr-C. Primers include restriction site, stop codon (*), sequences specific for the cleavage site (solid rectangle), and sequences specific for the 3' end of Vpr (open rectangle). The nucleotide sequences shown, with their Sequence Listing Identification Number in parentheses are those for: Vpr 17–24 (SEQ ID NO:4), Vpr 24/2 (SEQ ID NO:5), Vpr 2/7 (SEQ ID NO:6), Vpr 7/1 (SEQ ID NO:7), Vpr 1/6 (SEQ ID NO:8), Vpr TF/PR (SEQ ID NO:9), Vpr PR/RT (SEQ ID NO:10), Vpr RT/RNase H (SEQ ID NO:11), Vpr RT/IN (SEQ ID NO:12), and Vpr f (SEQ ID NO:13).

FIG. 5. Schematic representation of protease monomer and chimeric Vpr. (A) Structure of protease monomer (99 aa residues). Amino acid residues corresponding to the dimer interface region of active protease are indicated. (B) Structure of wild type (96 aa residues) and chimeric Vpr. Vpr-PC1 (100 aa residues) contains 4 amino acids from the C-terminus of protease added to the coding sequences of Vpr. Vpr-H-PC1 (105 aa residues) contains a flexible hinge region in between the Vpr and protease coding sequences. Theses constructs were generated in a plasmid vector designated pCDNA3 with the coding sequences of the Vpr chimera flanked by Hind III and Xho I restriction sites at the 5' and 3' end, respectively. The amino acid sequence shown with their Sequence Listing Identification Number in parenthesis are: PQIT (SEQ ID NO:23), TLNF (SEQ ID NO:24), and GGSSGTLNF (SEQ ID NO:25).

FIG. 8 is FIG. 8A plus FIG. 8B.

DETAILED DESCRIPTION OF THE INVENTION

Abbreviations

Figure 2A:
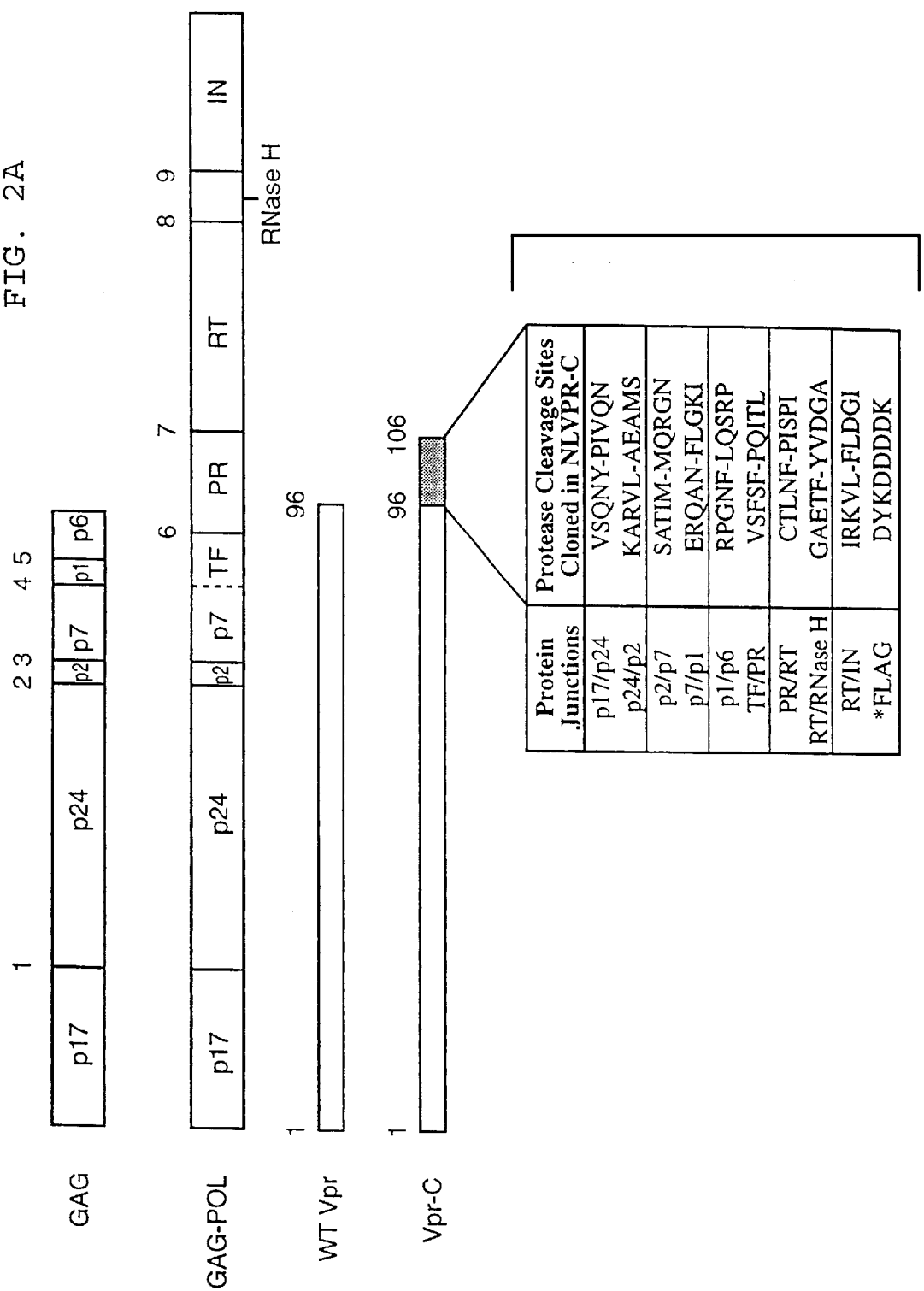
FIG. 2. (A) Schematic representation of the Gag, and Gag-Pol precursors of HIV-1 indicating protease cleavage sites 1–9 (bold). The Vpr-C proteins contain the corresponding cleavage signal found in the Gag and Gag-Pol precursors indicated by number and abbreviation for the site, fused in-frame to the C terminus of Vpr resulting in a protein of 106 aa. Likewise, all Vpr-C constructs received a Flag epitope (DYKDDDDK, Asp-Tyr-Asp-Asp-Asp-Asp-Tyr (SEQ ID NO:1)) immediately following the cleavage site. The asterisk indicated the construct containing the Flag epitope alone. The dashed line indicates site of ribosomal frame shift. The amino acid sequences shown, with their Sequence Listing Identification Number in parenthesis are those for: p17/p24 (SEQ ID NO:14), p24/p2 (SEQ ID NO:15), p2/p7 (SEQ ID NO:16), p7/p1 (SEQ ID NO:17), p1/p6 (SEQ ID NO:18), TF/PR (SEQ ID NO:19), PR/R7 (SEQ ID NO:20), RT/RNase H (SEQ ID NO:21), RT/IN (SEQ ID NO:22), and FLAG (SEQ ID NO:1). (B) Proviral clone pNL4-3 cleaved with EcoRI/Sal/I in Vpr coding region to allow insertion of EcoRI/XhoI generated fragment from Vpr-C (NLVRP-C). Vpr-C- derived fragments contain a stop codon (*) so sequences downstream of SalI are out of frame. NLVPR-C HYGRO contains an SV-Hyg$^r$ cassette in the env gene for selection of positive clones in single-round replication assay.

Vpr-C, chimeric Vpr; RT, reverse transcriptase; RIPA, radioimmunoprecipitation assay; SV40, simian virus 40; SV- Hyg$^r$, SV40 hygromycin gene cassette; MLV, murine leukemia virus. Where amino acid sequences are denoted by both the single letter codes for amino acids and the three letter codes for amino acids, and there is a discrepancy between the two, the single letter code is most likely the correct one.

Aspects of the Invention

In a most general aspect, the invention is a chimeric viral protein comprising:

1) a first protein of a virus; and
2) a polypeptide of said virus, said polypeptide joined by a peptide linkage to said first viral protein in said chimeric protein, said polypeptide not normally joined by said peptide linkage to said polypeptide in said virus or in cells infected by said virus.

The polypeptide is preferably not more than 40 amino acids in length, most preferably not more than 10 amino acids in length.

One aspect of the invention is a chimeric viral protein comprising:

1) a first protein of a virus, said first protein not compromising a site for cleavage by a proteolytic enzyme of said virus;
2) a polypeptide proteolytic cleavage site, of said virus, said cleavage site being a site for cleavage by a proteolytic enzyme of said virus;
   such that said first protein is covalently linked by a peptide linkage to said polypeptide proteolytic cleavage site.

In a particular aspect of the invention, the first protein of the virus is not a capsid protein of the virus.

In another particular aspect, the polypeptide proteolytic cleavage site corresponds to an amino acid sequence found in the Gag or Gag-Pol proteins of HIV.

In another aspect of the invention is a chimeric viral protein comprising:

1) a first protein of a virus, said first protein not being a protein that forms a dimeric proteolytic enzyme of said virus;
2) a dimer interface polypeptide sequence of an enzyme of said virus, said sequence being one by which monomers of said enzyme combine to form the active dimeric enzyme, such that said first protein is covalently linked by a peptide linkage to said dimer interface polypeptide sequence. For example, the enzyme can be selected from the group, protease, DNA polymerase, ribonucleotide reductase.

A peptide linkage may be a single peptide bond, a single amino acid or a peptide (preferably less than 100 amino acids in length). If the peptide linkage is an intervening amino acid, the amino acid is joined by a single peptide bond to the first viral protein and by a single peptide bond to the polypeptide proteolytic cleavage site or the dimer interface polypeptide sequence. If the peptide linkage is an intervening peptide, that intervening peptide is joined by a single peptide bond to the first viral protein and by a single peptide bond to the polypeptide proteolytic cleavage site or the dimer interface polypeptide sequence.

The chimeric protein is constructed so that it is not identical to a protein normally found in the virus or normally created by the virus nucleic acid upon infection of cells. "Normally" refers to the situation where the chimeric protein is not the result of human intervention, such as the creation by a human of a chimeric nucleic acid construct coding for the chimeric protein.

The chimeric viral protein is preferably one wherein the virus referred to is an animal virus or a human virus, more preferably a human virus, most preferably selected from the group: herpes simplex virus type I, herpes simplex virus type II, human cytomegalovirus, human virus type, human immunodeficiency virus (HIV). Another preferred group, one that partially overlaps the preceding group, are retroviruses, most preferably lentiviruuses.

In particular embodiments, a chimeric viral protein is one wherein the first protein of the virus is not a capsid protein of the virus.

A related invention is a nucleic acid construct comprising a nucleotide sequence coding for an aforementioned chimeric viral protein, especially a nucleic acid construct that is a DNA construct.

Another related invention is the process of interfering with the growth of a virus in an animal or human, said process comprising administering to the animal or human a nucleic acid construct comprising a necleic acid sequence coding for the aforementioned chemeric protein. In one embodiment of the process, the animal or human has not been infected with the virus. In another embodiment, of the process, the animal or human has been infected with the virus. For example, the construct is administered so as to become integrated into a cell of an animal or human, examples of cells being a bone marrow cell or blood cell, such as a lymphocyte.

EXAMPLES

Example 1

Materials and Methods for Example 2

Plasmids

Cloning of wild-type and Vpr-C was carried out using the pCDNA3 expression vector as described (31–35). DNA fragments were amplified through PCR using the proviral clone pNL4-3 with primers containing HindIII and XhoI at the 5' and 3' end of the Vpr coding region, respectively. Sequences corresponding to the protease cleavage site residues were added to frame (10 aa) to the C terminus of Vpr coding sequences as part of the minus strand primer (see FIGS. 1A and 2A). Sequences representing the Flag epitope (F) were also added to the C terminus of Vpr. All recombinant plasmids were verified by restriction enzyme cleavage DNA sequence analysis.

Figure 2B:
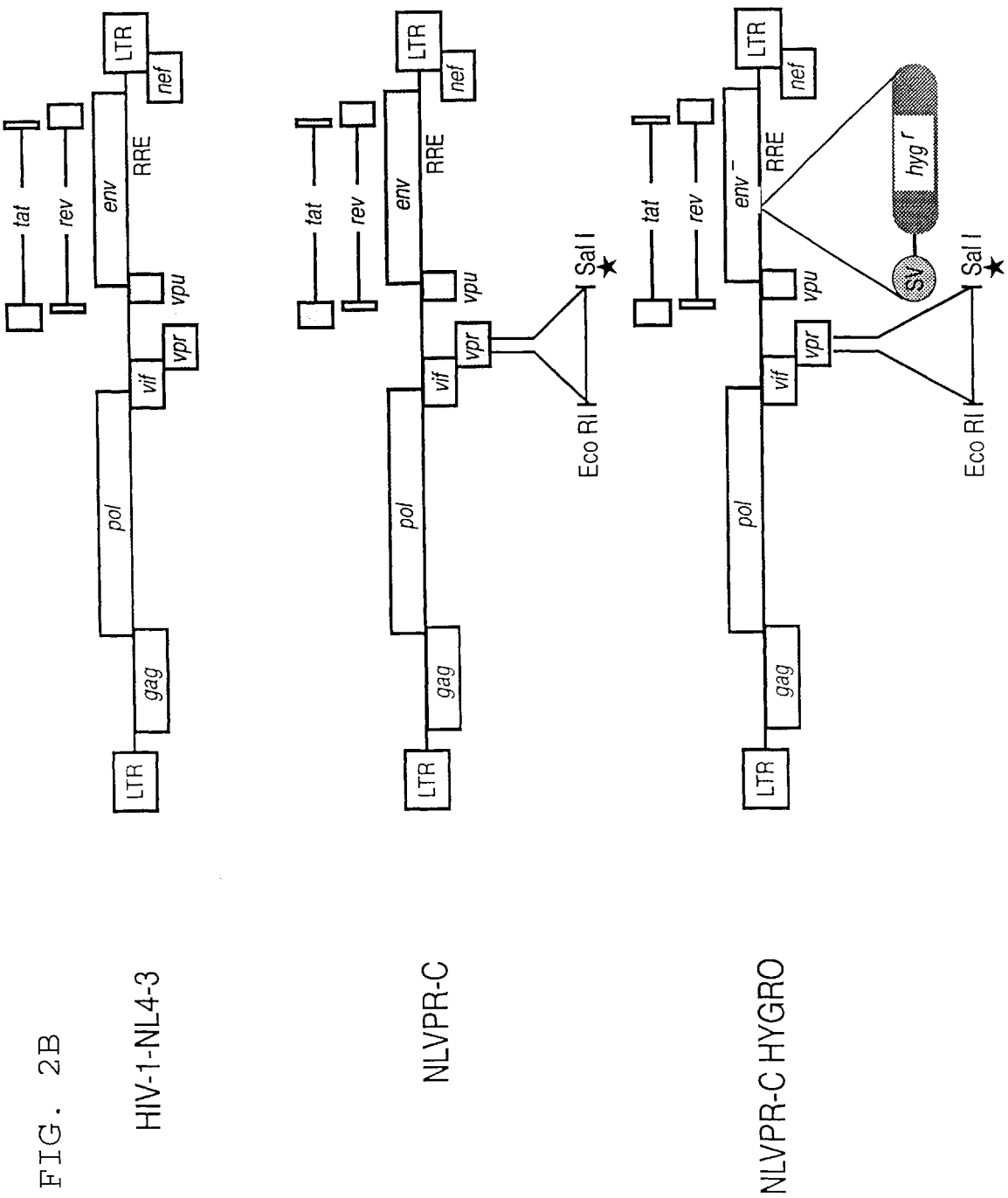

Vpr-C fragments were prepared by excision from the respective expression vector at the EcoRI and XhoI sites for insertion into the proviral DNA, pNL4-3, cleaved at the unique sites EcoRI and SalI (see FIG. 2B). This strategy does not interfere with the overlap region of vif and tat.

In Vitro Transcription/Translation and RIA Analysis of Vpr-C Proteins

The coupled T7 transcription/translation system (Promega) was used for characterizing the expression of the Vpr-C clones. Incubation conditions were followed according to manufacturer's instructions.

Radioimmunoprecipitation assay (RIPA) analysis if in vitro translated proteins was carried out using polyclonal antiserum to Vpr as described (35).

Infection/Transfection, Metabolic Labeling, Immunoprecipitation, and Western Blot Analysis For expression studies, the recombinant vaccinia virus vTF7-3 that expresses T7 RNA polymerase in infected cells was used. HeLa cells at $10^6$ cells per 35-mm tissue culture dish were first infected with the virus at a multiplicity of infection of 10 for 1 hr and subsequently transfected via the Lipofectin method (Life Technologies, Gaithersburg, Md.) with the Vpr-C expression vectors in conjunction with an HIV-1 Gag expression vectors for virion incorporation analysis. Transfected cells were washed in PBS and starved in DMEM (without sera, Met and Cys) for a total of 1 hr, followed by labeling with $^{35}S$ protein labeling mix (Du Pont/NEN) at 200 $\mu$Ci/ml (1.2 Ci/mmol; 1 Ci=37 GBq) for a total of 5 hr. The culture medium, cleared of cellular debris by low speed centrifugation, was subsequently centrifuged at 25,000 rpm for 90 min, and virus-like-particles were suspended in RIPA buffer. Cells were washed twice in PBS and lysed in RIPA buffer as above. Immunoprecipitation analysis subsequently followed using polyclonal HIV-1 Vpr, Gag, and Flag epitope antibodies, respectively. Immunoprecipitated proteins were seperated on 15% SDS/PAGE and immunoblot analysis was carried out as described (Santa Cruz Biotechnology).

Generation of Virus upon Transfection of HIV-1 Proviral DNA and Virus Infectivity Studies Both wild-type-and Vpr-Ccontaining proviral DNA were transfected into rhabdomayosarcoma cells as described (40). Virus particles released into the culture medium were harvested 72–120 hr posttransfection and quantitated by RT and p24 antigen assay (40). The virus infectivity studies were carried out using established $CD4^+$ CEM cells as targets. Three million cells were incubated with virus innoculum, normalized on the basis of RT activity or p24 antigen levels, for 2 hr at 37° C. Infected cells were then washed and resuspended in RPMI 1640 medium. Aliquots from infected cultures were take once a week and split to keep the cell concentration at one million cells/ml.

Single Cycle Replication Assay

Using a previously published strategy, proviral DNAs containing Vpr-C were cleaved with the NheI restriction endonuclease, and a simian virus 40 (SV40) early promotor/enhancer hygromycin gene cassette (SV-Hyg$^r$) was inserted, leading to the disruption of the env gene (41–43). pED84, which contains the insertion of the SV-Hgy$^r$ cassette in the env gene of pNL4-3 was used as the control plasmid for transfection experiments and contains a wild-type vpr gene (44). To generate virus particles capable of only a single round of replication, cotransfection of Cos cells was performed with the Vpr-C modified proviral clones (NLVpr-C-HYGRO) and an amphotropic murine leukemia virus (A-MLV) envelope glycoprotein (Env-gp) expression plasmid, pSV-A-MLV-env (see FIG. 2B) (45).

Virus particles released into the medium were harvested 72 hr posttransfection and cleared of cellular debris by low speed centrifugation. An aliquot was used to infect HeLa T4 cells. At 48 hr postinfection, selection of hygromycin resistance was initiated with media containing 200 mg/ml hygromycin B. After 9–11 days, hygromycin-resistant colonies were stained with 0.5% crystal violet in 50% methanol and counted.

Example 2

Results

Construction of Vpr-C Containing HIV-1 Protease Cleavage Signal Sequences

The structural proteins Gag and Gag-Pol of HIV-1 are synthesized as precursor polyproteins and contain a total of 12 cleavage sites recognized by the virus-encoded protease allowing for precursor processing and virus maturation (46). The specificity of HIV-1 protease is found to lie in the detection and cleavage of a scissile bond (Met-Met, Leu-Ala/Phe, Tyr-Pro, Phe-Pro/Tyr/Leu) within the minimim context of four residues 5' (P1–P4) and three residues 3' (P1'–P3') to the site of cleavage (2, 47–49). In this study, nine major sites for generating Vpr-C were selected. Primers that comprise sequences corresponding to the nine cleavage sites, followed by a termination codon, were synthesized to allow for the addition of sequences at the C terminus of Vpr by PCR (FIG. 1). In addition, following each of the cleavage sites, and 8 aa Flag epitope was added to aid in antibody detection of the chimeric proteins (23). As a control, we have generated a Vpr-C containing only a Flag epitope at the C terminus. The proviral clone pNL4-3 was used as the template for generating replication-competent proviral clones containing the Vpr-C. The details of cleavage site residues used for generating Vpr-C are presented in FIG. 2A. The designation of Vpr-C is indicated by the abbreviation for the respective protease cleavage site. The cleavage signals added onto our Vpr-C proteins include the P5 and P5' residues specific to each of the respective sites, Vpr-C clones were verified for sequence integrity.

Expression and Virion Incorporation of Vpr-C

Figure 3:
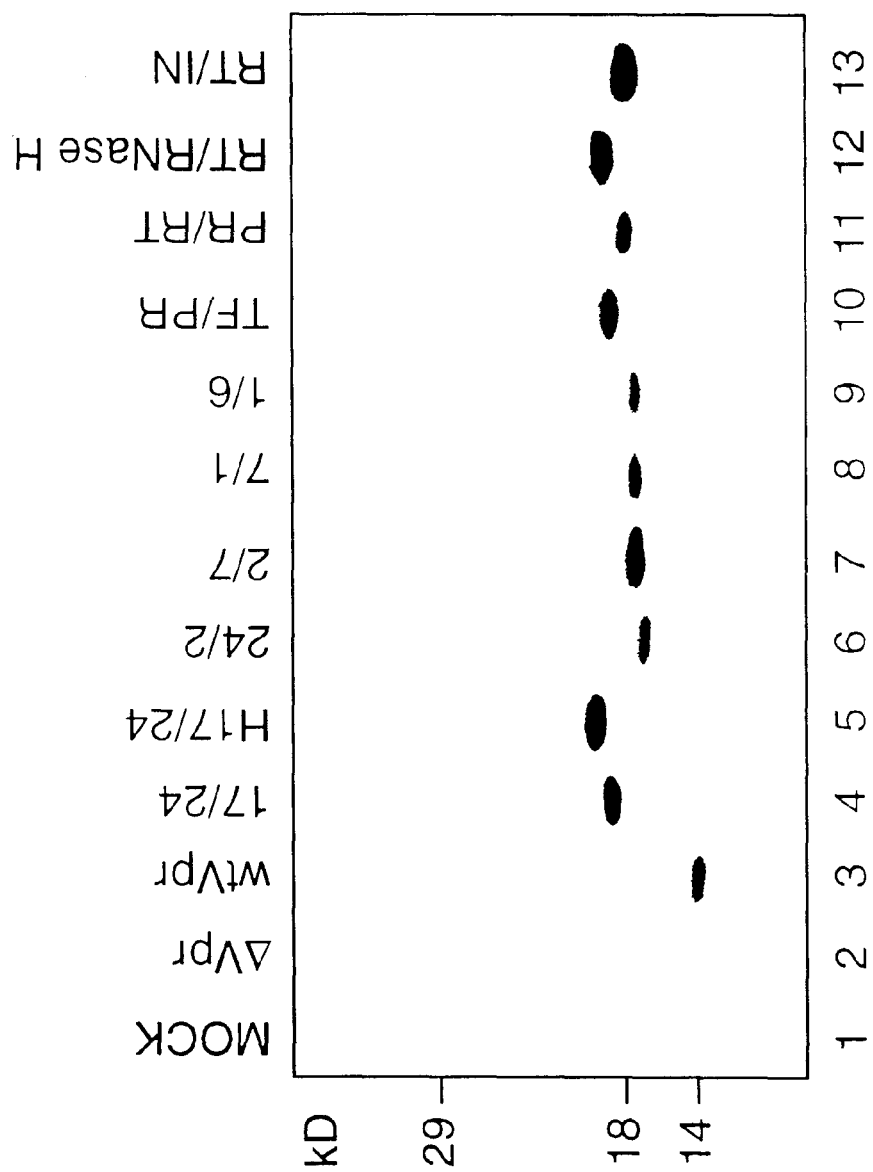
FIG. 3. RIPA analysis of in vitro transcribed and translated Vpr-C proteins. Antiserum to Vpr was used as described. Vpr-C proteins exhibit a shift in migration and appear around 18 kDa. Designation of the Vpr constructs are described in legend to FIG. 2.

We used an in vitro T7 expression system to verify the expression of each of the Vpr-C proteins. In vitro translated Vpr-C proteins were immunoprecipitated with polyclonal Vpr antiserum. As expected, each Vpr-C protein was expressed at levels equal to the wild-type Vpr protein (FIG. 3). As reported earlier, the wild-type Vpr migrates to 14 kDa (32). The different Vpr-C proteins displayed altered mobility in comparison to wild-type Vpr. This may be due to the added signal sequences containing highly acidic and hydrophobic residues. The Vpr-C Flag protein (Vpr-F) with the Flag addition, made mostly of acidic residues, also migrated differently than wild-type Vpr (data not shown).

Figure 4A:
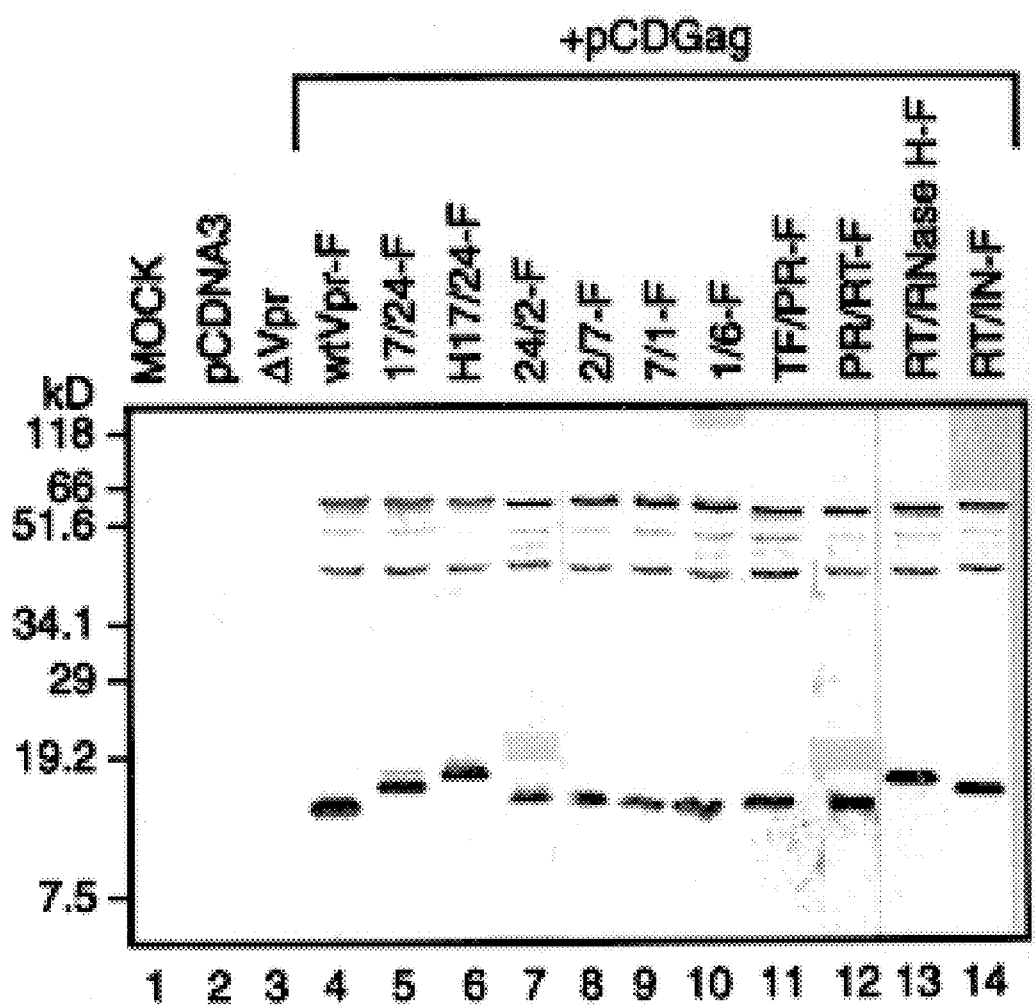
FIG. 4. Immunoblot analysis of HeLa cells transfected with Vpr-C constructs. (A) Analysis of cell lysates showed that Vpr-C and Gag proteins are produced and migrate to the expected 18-kDa and 55-kDa positions, respectively. Observed on the original photos of the gels, but not necessarily on reproductions of those photos, were weak bands as follows: For each of 7/1-F, 1/6-F, TF/PR-F, a single weak band between the band migrating between the 51.6 and 66 kD markers and the major band migrating roughly mid way between the 34.1 kD marker and the 51.6 marker. (B) Analysis of cell supernatants revealed that the Vpr-C retains its ability to be incorporated into virus-like particles. Observed on the original photos of the gels, but not necessarily on reproductions of those photos, were weak bands as follows: In the lane for 24/2-F, three weak bands for proteins with molecular weights slightly less than 66 kD, migrating close to the 51.5 kD marker; In the lane for 7/1-F, a very weak band close to the 51.6 kD marker and a weak band mid way between the 34.1 and 51.6 markers, and for TF/PR-F, 5 weak bands ranging from about the 51.6 marker to close to the 34.1 marker.

To verify that the Vpr-C proteins retain the ability to incorporate into virus-like particles directed by HIV-1 Gag and to monitor the expression of Vpr-C in cells, we employed a vaccinia virus T7 RNA polymerase expression system (vTF7-3). vTF7-3-infected HeLa cells were transfected with wild-type Vpr or Vpr-C expression plasmids containing the Flag epitope (F) in combination with the Gag expression vector pCDGag by the Lipofectin method. Immunoblot analysis of Vpr-F, Vpr-C-F, and Gag was performed in both cells lysates and culture media with anti-Flag and anti-Gag antiserum 24 hr posttransfection (FIG. 4). Results of the cell lysate showed the presence of both Gag and Vpr (FIG. 4A). The culture medium immunoblot indicated that the Vpr-C proteins are incorporated into virus-like particles (FIG. 4B). As expected, the mock, control plasmid pCDNA-3 and pCDVprΔ cells failed to show a corresponding protein.

Effect of Vpr-C in HIV-1 Infection of CEM Cells

Upon characterization of Vpr-C constructs, the Vpr-C protein coding sequences were introduced into HIV-1-NL43 proviral DNA (NLVpr-C) (FIG. 2B). To avoid disruption of the overlap of vpr with tat at 3' end in the pNLVpr-C construct, the unique EcoRI and Sal/I restriction endonuclease cleavage sites were used to introduce the 3' end of chimeric Vpr from the recombinant plasmids.

The proviral DNA NL4-3 and NL-Vpr-C were transfected into rhabdomayosarcoma cells to generate viruses for evaluating the effect of Vpr-C at the level of viral replication. Virus released into the medium was collected 5 days post-transfection and quantitated by an RT assay (40). Equivalent RT activity infected cells were monitored for virus replication for nearly 30 days. Cultures infected with wild-type pNL4-3 showed peak virus production at 15–21 days postinfection, as is generally observed with a spreading infection. Similar results were noted using virus derived from pNL4-3 Vpr-F (data not shown). The replication of the virus particles derived from proviral DNA containing NL-Vpr-C was altered in comparison to the control (Table 1). The chimeric viruses exhibited a delayed kinetics of virus spread and very little replication was evident for up to 14 days, suggesting the presence of a mixture of infectious and noninfectious virus particles. Strikingly, the NLVpr-24/2 virus showed no viral replication for up to 28 days. In general, the infectivity assays carried out in CEM cells represent a spreading infection and the results generated may reflect a cumulative effect over multiple rounds of infection.

Utilization of Single-Round Replication Assay to Evaluate the Effect of Vpr-C

To precisley evaluate the effect of Vpr-C in a single cycle of virus replication a single-round replication assay was established as described (41–44). For this purpose, NL4-3 and NL4-Vpr-C proviral DNA were cleaved at the NheI restriction enzyme cleavage site where a hygromycin gene cassette (SV-Hyg$^r$) under the control of the SV40 early promoter was inserted (NLVpr-CHYGRO) (FIG. 2B) because the SV-Hyg$^r$ cassette was inserted in the env gene leading to the disruption of Env expression, virus particles containing amphotropic envelope were generated by trans-complementation using the MLV envelope expression plasmid by cotransfection.

The virus particles present in the supernatant were used to infect HeLa T4 cells and the infected cells were selected in media containing hygromycin B as described (41–44). The number of Hyg$^r$ resistant colonies in the presence of the antibiotic reflects the ability of a pseudotyped particle to infect and integrated into the cellular genome. The results are presented in Table 2 and correlated well with the multiple rounds of replication assay.

In an attempt to increase the efficiency of Vpr-C as pseudosubstrates for protease, we have introduced amino acids constituting a flexible hinge region (Gly-Gly-Ser-Ser-Gly (SEQ NO:2)) immediately 5' to the cleavage signal of the 17/24 construct (FIG. 2A). This construct was chosen to receive a hinge based

TABLE 1

Effect of Vpr-C on virus Replication

| Virus derived from | RT activity in culture supernatant, cpm/µl | | |
|---|---|---|---|
| designated proviral DNA | 14 days after infection | 21 days after infection | 28 days after infection |
| pNL43* | 1082 | 1678 | 1380 |
| NLVpr 1/6 | 49 | 219 | 828 |
| NLVpr 24/2 | 0 | 67 | 0 |
| NLVpr 2/7 | 287 | 1883 | 1755 |
| NLVpr PR/RT | 29 | 2845 | 2450 |
| NLVpr 17/24 | 28 | 2133 | 1366 |
| NLVpr RT/RNase | 193 | 2116 | 1248 |
| NLVpr 7/1 | 299 | 1965 | 2132 |
| NLVpr TF/PR | 681 | 652 | 1016 |

*The replication pattern of virus derived from NLVPR-F was similar to pNL4-3.

TABLE 2

Effect of Vpr-C in a single round replication

| Proviral Vpr clones | Titers CFU/ml* | % (+) inhibition | % (+) up-regulation |
|---|---|---|---|
| ED84 | 1536 | | |
| NL 1/6 | 1088 | 30 | |
| NL 2/7 | 928 | 40 | |
| NL H 17/24 | 1088 | 30 | |
| NL PR/RT | 2608 | | 169 |
| NL TF/PR | 1072 | 31 | |
| NL 17/24 | 1248 | 29 | |
| NL 7/1 | 1936 | | 126 |
| NL 24/2 | 0 | 100 | |

*NO Hygr colonies were observed for any of the proviral clones when the trans-complementation was preformed without pSV-A-MLV-env, pSV-A-MLV-env by itself, or mock transfected.
*Extent of inhibition and upregulation was calculated in comparison to pED84 control proviral DNA.
*The virus derived from NLVPR-F proviral DNA showed replication results similar to virus from pED84.

on its weak performance and from previous reports that the Tyr-Pro scissile bond it contains acts as a late site for cleavage making it one of the less efficient sites for protease cleavage (50). Results generated from the H17/24 chimera indicated an enhancement of the inhibitory affect in the single round infection assay; however, it still lacks the total inhibition seen with Vpr-24/2.

Discussion

Currently, there are several drugs that have been approved by the Federal Drug Administration to treat HIV-1 infected individuals, all of which either target the viral RT or protease enzymatic activities of the virus. The continued treatment of virus-infected individuals with these drugs has led to the identification of viruses that exhibit partial to full resistance to treatment as a result of specific changes in the target enzymes (51). In the absence of a successful vaccine to prevent HIV-1 infection, various alternative approaches have been proposed and are being actively investigated (8–11). These include the capsid fusion approach where a toxic gene product can be fused to the capsid protein for inactivating the virion components, chimeric receptor molecules targeted to Env, and the use of trans-dominant mutants targeting Gag, Rev, Tat, and Env for inactivating the virus at different stages of the life cycle (52–57).

The virion association of nonstructural proteins encoded by HIV-1 provides a unique opportunity to attack the virus particle in trans, and are advantageous over structural protein based antiviral approaches (52–54, 57). Along these lines, Kappes and coworkers (35, 58, 59) have generated chimeric proteins based on HIV-1 Vpr and HIV-2 Vpx utilizing stapylococcal nuclease and wild-type and mutated HIV-1 protease fused in-frame to these proteins. In our studies, we have generated a chimeric protein based on Vpr utilizing the conserved protease cleavage site sequences from the Gag and Gag-Pol precursor polyproteins as a fusion partner. These sequences are efficiently cleaved by HIV-1 protease when presented as peptide substrates (46–49, 60). The interesting features of the chimeric proteins generated here are the minimal addition of residues (10 residues), no toxicity due to added sequences, and the likelihood of Vpr-C to behave like the wild-type Vpr protein due to the minimal increase in size. The strategy outlined here brings the chimeric protein closer to the target protein in the virus particle. It is likely that the ability of Vpr-C to serve as a pseudosubstrate for HIV-1 protease can lead to the exhaustion of protease activity. This would, in essence, reduce the effectiveness of protease to participate in the maturation of the virus particle by not acting on the bona fide viral precursor proteins.

The results generated with Vpr-C showed that the chimeric protein retains the ability to get incorporated into the virus particle. In the context of the proviral DNA, the Vpr-C suppressed HIV-1 replication both in multiple- and single-round replication assays. As the single-round replication assay involves the establishment of cells resistant to hygromycin, one concern was whether the wild-type Vpr or Vpr-C would complicate the results due to cell cycle arrest. This does not seem to be the case due to the positioning of the selectable marker (hygromycin gene) which is under the control of the SV40 promoter. The concordance between the results from the single- and multiple-round replication assays also argues against such a possibility. In addition, further support for such an interpretation is seen with the variable replication results observed with the different Vpr-C containing viruses.

Considering the stability of chimeric vpr sequences in the viral genome over several rounds of replication (data not shown), the kinetics of the replication pattern suggests that the viral population may contain a mixture of replication competent and defective viruses. Suprisingly, we noted that some Vpr-C proteins did not have influence on viral replication ans some even showed an up-regulation of viral replication (Tables 1 and 2). Complete inhibition was observed only with the Vpr chimera 24/2 and moderate inhibition was observed with Vpr chimeras 1/6, 2/7, 17/24, and trans-frame (TF)/PR. The cleavage of the 24/2 site is important in that it serves as a regulator for the sequential processing of the Gag precursor, and is unique in that it is the only site of the nine recognized by the protease to have glutamic acid at the P2' position (61).

The inhibition of viral replication observed with viruses containing Vpr-C may be due to the ability of Vpr-C to overwhelm the protease activity. Biochemical analysis of virus particles with respect to the status of the precursor proteins is likely to provide information regarding the mechanism of inhibition. Earlier biochemical studies showed that 2,500 Gag and ~5–10% of Gag-Pol molecules in relation to Gag are present in each virion (1,31). Though the exact number of Vpr molecules present in the virus particle has not been determined for HIV-1, studies on HIV-2 indicate that Vpx, a protein related to Vpr, is present in equimolar concentration to that of p28 in virus particles (62). Such a scenario in HIV-1 is likely to lead to the presence of an enormous number of Vpr-C pseudosubstrates for protease to act on within the virus particle and may interfere with the processing of the authentic viral precursor proteins. It has been shown that partial inhibition of Gag and Gag-Pol processing results in aberrantly assembled viruses (2). The variable inhibition we observed regarding viral replication suggests that the ability of Vpr-C to serve as a pseudosubstrate for protease may vary as observed with oligopeptide substrates corresponding to cleavage sites (46, 47,50,60,63). Furthermore, previous work on protease cleavage in the context of corresponding peptides and protein precursors has revealed the importance of either residues or conformational determinants within the Gag and Gag-Pol precursors that affect the order of cleavage and the actual cleavage event of the target substrates (50,61,64,65). Because the cleavage signals in Vpr-C are presented out of the context of the Gag precursors, the absence of both up and downstream determinants may have prevented Vpr-C from being a substrate and competitor for the protease cleavage site. This would ultimately lead to the lack of influence on viral maturation and infectivity.

The threshold level of protease required for maturation of the virus particle is not known. Studies involving protease inhibitors have shown that the enzyme needs only a 50-fold reduction in activity whereas a 25-fold reduction still allows for processing and subsequently the production of infectious virus (66). It is plausible that the constructs showing no effect did not offer enough competition to prevent processing from occurring. Likewise the partial inhibitory constructs may not have reached the 50-fold reduction threshold, but went farther than those chimeras with no apparent effect. The high level of replication observed with virus derived from certain Vpr-C containing proviral DNA is intriguing. Because equal amounts of virus were used as innoculum to infect CEM cells, it is likely that some Vpr-C pseudosubstrates enhanced the level of virus production by activating protease. Alternatively, the increased protease activity may act on an as yet unidentified step in viral replication.

We have shown that a novel class HIV-1 agents can be generated with the desirable end result of eliminating virus infection. We have termed this class of agents, "anti- HIV agents from within". The studies carried out with the virus derived from proviral DNA containing Vpr-C provided evidence in support of this strategy. The disadvantage in the use of Vpr as fusion partner for generating a chimeric protein is its ability to arrest cells at the $G_2$ stage of the cell cycle. In this regard, work from our laboratory and others (ref. 22) has demonstrated the the cell cycle arrest can be abolished by introducing changes at the C terminus of Vpr, and yet still retain virion incorporation. In addition, the Vpr-C proteins will also prove to be useful for dissecting the steps involved in virus maturation.

These results show that chimeric proteins generated from within HIV-1 have the ability to suppress HIV-1 replication and make ideal agents for gene therapy or intracellular immunization to treat HIV-1 infection.

We would like to express our thanks to Dr. Antiono Panganiban (University of Wisconsin, Md.) for the gift of pED84. pSV-A-MLV-env was obtained from the AIDS Research And Reference Reagent Program of the National Institute of Health.

Example 3

Materials and Methods for Example 4

Recombinant Plasmids

Construction of the Vpr expression plasmid was carried out as described (Mahalingam et al., 1995a–e). Vpr coding sequences were amplified using primers containing Hind III and Xho I restriction enzyme recognition sequences at the 5' and 3' end, respectively. The DNA fragment generated through PCR was cloned into a pCDNA3 plasmid vector. For the generation of the chimeric construct containing Vpr and the C-terminus of PR, four aa residues from the C-terminus corresponding to the dimer interface structure of PR were added in frame to the C-terminus of Vpr (Vpr-PC1). A similar strategy was also used for the construction of the Vpr-H-PC1 plasmid, in which a flexible hinge region was added (The 5-amino acid sequence G-G-S-S-G, as represented by the standard single-letter codes for amino acid; Gly-Gly-Ser-Ser-Gly (SEQ ID NO:2)) between the Vpr coding sequences and the dimer interface domain. All of the recombinant plasmids were verified by DNA sequence analysis.

The chimeric Vpr sequences were introduced into the HIV-1 proviral DNA designated NL4-3 (Adachi et al., 1986). The DNA fragment encompassing the 3' end of the chimeric Vpr generated by cleavage with EcoR I and Xho I from the expression plasmid was cloned into the proviral DNA, cleaved at the unique EcoR I and Sal I site. This strategy does not interfere with the overlap of vpr and tat, as the Vpr fragment contains a termination codon.

Expression and Incorporation Into Virus-like Particles

The expression of the Vpr-PC1 and Vpr-H-PC1 proteins was analyzed using an in vitro transcription-coupled translation system in accordance with the manufacturer (Promega). The translated protein was subjected to radioimmunoprecipitation (RIPA) as described (Mahalingam et al., 1995d). For the expression of Vpr in cells, and Vpr incorporation into virus particles, we have used the vaccinia virus T7 polymerase system (Mahalingam et al., 1995a–e). Vpr and Gag expression plasmids were transfected alone and in combination into HeLa cells. Cell lysates and culture supernatants were subjected to RIPA using antibodies to Gag and Vpr as previously described (Mahalingam et al., 1995d.)

Virus Infection Studies

Proviral DNA containing Vpr, Vpr-PC1, Vpr-H-PC1, or other chimeric Vpr was transfected into RD or HeLa cells. Virus released in the culture medium was collected at the end of 72–120 hours and quantitated by an RT assay (Nagashunmugam et al., 1992). An equivalent amount of virus based on RT activity values was used to infect the CEM cells for viral replication studies. The culture supernatant from infected cells was monitored periodically for virus production.

Single Cycle Replication Assay

The chimeric Vpr containing proviral DNA (NLVpr-PC1 and NLVpr-H-PC1), or wild type NL4-3 DNA, was cleaved at the Nhe I site and a Hygr gene under the control of SV40 early promoter was inserted into env which disrupts its expression. Co-transfection of the modified proviral DNA and the murine amphotropic env expression plasmid results in the generation of virus particles capable of only a single round of replication (Rizvi et al., 1996). The virus particles released into the culture supernatant were centrifuged, resuspended in medium from which an aliquot was used to infect HeLa cells in the presence of DEAE-dextran. The infected cells were washed 48 hours after infection and placed in medium containing hygromycin. At the end of 14 days, colonies of cells resistant to hygromycin were stained and counted. In addition, the infectivity of the virus particles was also tested by using a MAGI assay as described (Kimpton and Emerman, 1992). This assay provides a measure of infection of a cell by the induction on an endogenous P-galactosidase gene under transcriptional control of the HIV-1 LTR.

Electron Microscopy (EM)

After transfection, cells were fixed for EM with 2.5% glutaraldehyde, postfixed with osmium tetroxide and embedded in Epon/Araldite. Sections were then stained with lead citrate and uranyl acetate (Nagashunmugam et al., 1992).

Example 4

Results

Chimeric Vpr Maintains the Phenotype of the Wild-type Vpr Protein

Based on structural and enzyme inhibition studies involving peptides derived from HIV-1 PR, we fused the C-terminal four residues (TLNF, Thr-Leu-Asn-Phe) of protease in frame to the C-terminus of Vpr (FIG. 5) designated Vpr-PC1. There is a possibility that the PR coding sequences present in Vpr-PC1 may not be accessible to its target Gag-Pol and/or partially cleaved precursor proteins due to the direct fusion to the C-terminus of Vpr. In order to give flexibility to the residues added to the vpr, an additional construct was generated where a flexible hinge region was introduced between Vpr and TLNF (Vpr-H-PC1). For the generation of a negative control, residues unrelated to PR from the protein kinase domain (PKA) (R-R-A-S-V, Arg-Arg-Ala-Ser-Val (SEQ ID NO:3)) and the FLAG epitope (D-Y-K-D-D-D-D-K, Asp-Tyr-Asp-Asp-Asp-Asp-Tyr) were fused in-frame with the C-terminus of Vpr.

Figure 6:
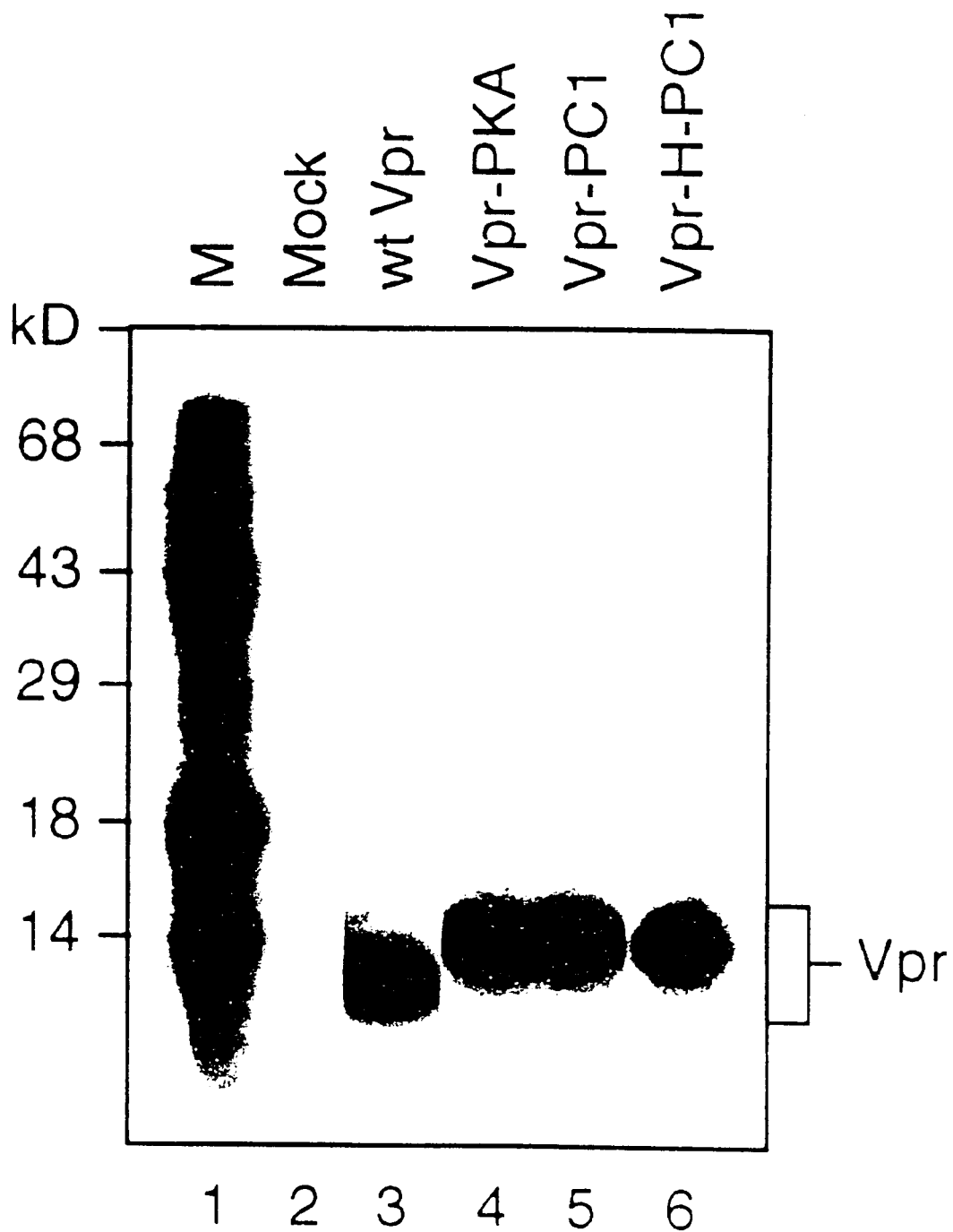
FIG. 6. RIPA analysis of in vitro-translated Vpr, Vpr-PC1, and Vpr-H-PC1 proteins. Antiserum against full-length Vpr was used. Details of Vpr-PC1 and Vpr-H-PC1 are as described in FIG. 5. As expected, the pCDNA3 vector alone did not show a band in the 14 kDa range as was observed with the wild type Vpr plasmid.

The characteristics of Vpr-PC1 and Vpr-H-PC1 (chimeric Vpr) (SEQ ID NO:1) says were then tested using an in vitro transcription-coupled translation system. The translated protein was immunoprecipitated utilizing antibodies to full-length Vpr as described (Mahalingam et al., 1995a). The Vpr-PC1 and Vpr-H-PC1 vectors showed proteins with altered migration in comparison to the wild type Vpr in the gel, which may be due to the addition of amino acid residues at the C-terminus (FIG. 6).

Figure 7:
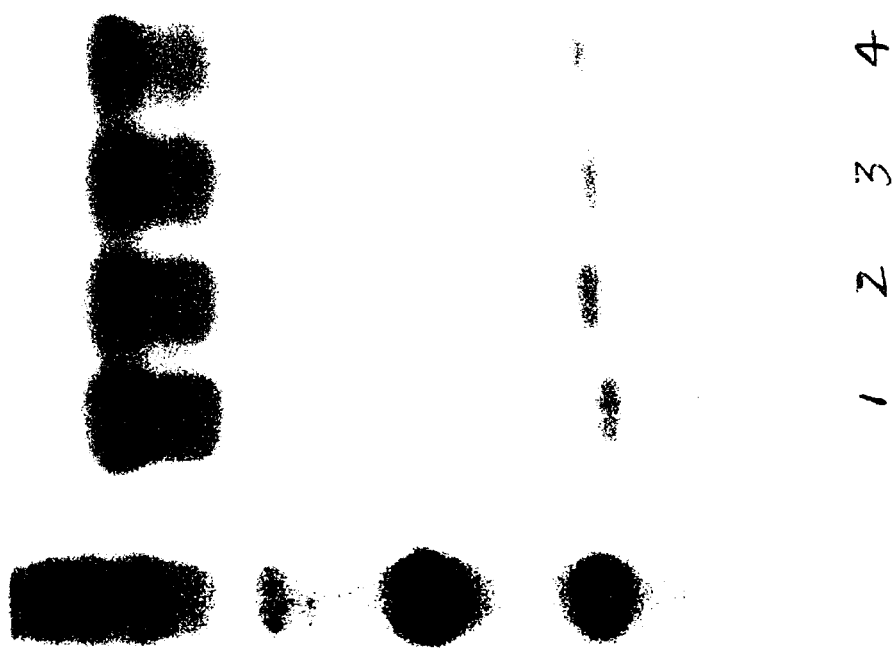
FIG. 7. Incorporation of chimeric Vpr into virus-like particles directed by HIV-1 Gag as described in materials and methods. Analysis of cell supernatants of transfected HeLa cells revealed that Vpr-PKA,Vpr-PC1 and Vpr-H-PC1 retained the incorporation phenotype of wild-type Vpr. (lane 1), wt Vpr; (lane 2), Vpr-PKA (control); (lane 3), Vpr-PC1; and (lane 4), Vpr-HPC1.

Since incorporation of chimeric Vpr proteins into virus particles is vital to our strategy, we analyzed the virion incorporation properties of Vpr-PC1 and Vpr-H-PC1, using the recombinant vaccinia virus containing T7 polymerase to drive protein expression as described (Mahalingam et al., 1995a–e). Co-transfection of Gag and Vpr, Vpr-PKA, Vpr-PC1, or Vpr-H-PC1 plasmids into vaccinia virus infected Hela cells showed expression of appropriate proteins within cells. Analysis of the virus-like particles released from cells by RIPA indicated two bands corresponding to Gag and Vpr (FIG. 7). Thus, It is evident that the Vpr-PC1 and Vpr-H-PC1 proteins retain the ability to be incorporated into virus particles.

Effect of Chimeric Vpr on HIV-1 Replication

Figure 8B:
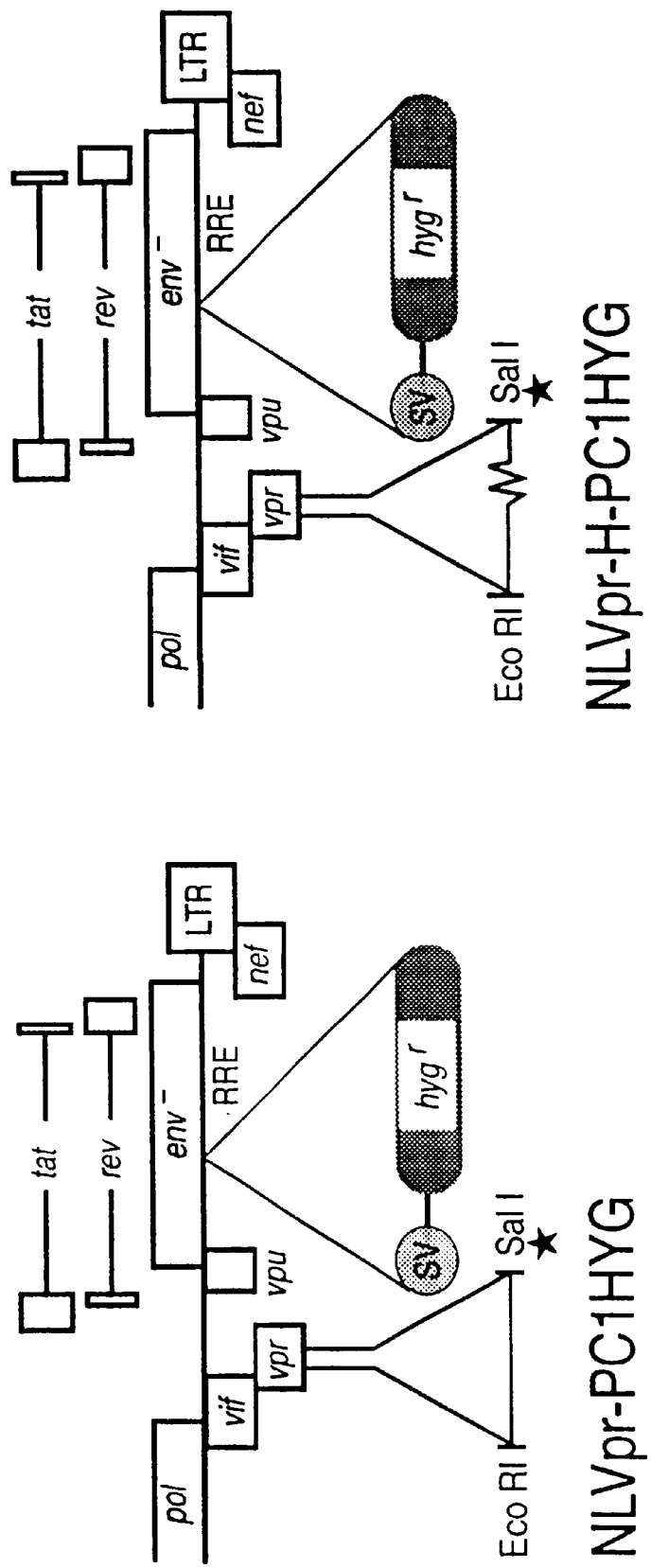
FIG. 8. Generation of HIV-1 proviral DNA containing Vpr-PC1 and VprH-PC1 sequences. Proviral clone-designated NL4-3 was cleaved with EcoRI/Sal I in Vpr coding region to allow insertion of EcoRI/Xho I from VprPC1 or Vpr-H-PC1. Since the fragment generated with EcoR I and Xho I from Vpr-PC1 and Vpr-H-PC1 carries a termination codon following the coding sequences, the duplication of sequences created in the proviral DNA is not translated. It is also important to note that the strategy used here does not interfere with the overlapping region of vpr and tat coding sequences. NLVpr-PC1-HYGRO and NLVpr-H-PC1 HYGRO contain an SV40-Hygr cassette in the env gene for selection of positive clones in a single-round replication assay. The wild-type, Vpr-PC1 and Vpr-H-PC1 containing proviral DNAs were cleaved with the Nhe I restriction enzyme, and a Hygr cassette under the control of the SV40 early promoter was introduced thus eliminating env gene expression.

To evaluate the effect of Vpr-PC1 and Vpr-H-PC1 on viral replication, we have generated HIV-1 proviral DNA containing the sequences encoding chimeric Vpr. We have used HIV-1 proviral DNA (designated NL4-3) for this purpose, as it contains all the functional auxiliary genes encoded by the virus (Adachi et al., 1986). Vpr-PC1 and Vpr-H-PC1 coding sequences were cleaved using EcoR I and Xho I restriction enzymes, and the released fragment was ligated to the proviral DNA cleaved with EcoR I and Sal I (FIG. 8). The chimeric Vpr in the proviral DNA was verified by DNA sequence analysis.

The proviral DNA containing Vpr-PC1 and Vpr-H-PC1 was transfected into either human rhabdomyosarcoma (RD) or HeLa cells to generate viruses for biological studies. The virus particles were quantitated by RT and/or HIV1 p24 antigen assays with subsequent infection (viral replication assay) being carried out using established CD4+ CEM cells as targets. The virus infection was initiated with an equal amount of virus based on RT activity, with infected cells being monitored for up to a month. The virus derived from wild type NL4-3 replicated as expected, with a peak virus production at 15–20 days after infection. In contrast, the replication studies carried out with the viruses derived from proviral DNA containing Vpr-PC1 or Vpr-H-PC1 showed a delayed kinetic pattern and registered a low level of virus production in comparison to the control (Table 3). These results suggest that viruses generated from Vpr-PC1 and Vpr-H-PC1 containing proviral DNA may harbor a mixture of non-infectious and infectious particles. The viral replication assay using CEM cells involves a spreading infection, which needs to be considered when interpreting the observed results. Subsequently, this assay does not allow the effect of Vpr-PC1 and Vpr-H-PC1 to be evaluated quantitatively when a mixture of viral populations exists.

Therefore, to precisely quantitate the effect of Vpr-PC1 and Vpr-H-PC1 on viral replication, we used a single-round replication assay. Limiting the virus to a single replication event would allow one to observe direct and immediate effects of the chimeric proteins on the infectivity of the virus produced. Co-transfection of NLVpr-PC1-HYGRO or NLVpr-H-PC1-HYGRO, in which the endogenous env is disrupted with a hygromycin (Hygr) resistance gene/marker under SV40 promoter, with an amphotropic Env expression plasmid into cells, resulted in the release of virus particles capable of initiating infection (FIG. 8). However, the viruses generated are replicationdefective due to the absence of a trans-complemented env gene in the target cells. The cells will confer resistance to hygromycin when grown in the selective medium if they contain the proviral DNA, possible only if successful infection occurred. In this assay, each Hygr colony of HeLa cells represented an infection event. When the numbers of colonies were compared to the control, the virus derived from NLVpr-PC1 and NLVpr-HPC1 registered an inhibition of 66 and 80%, respectively (Table 4). Likewise, when the virus particles were tested using another single cycle assay based on β-galactosidase expression, the MAGI assay, the results confirmed the earlier findings by showing 82 and 92% inhibition for NLVpr-PC1 and NLVpr-HPC1, respectively (data not shown).

Figure 9:
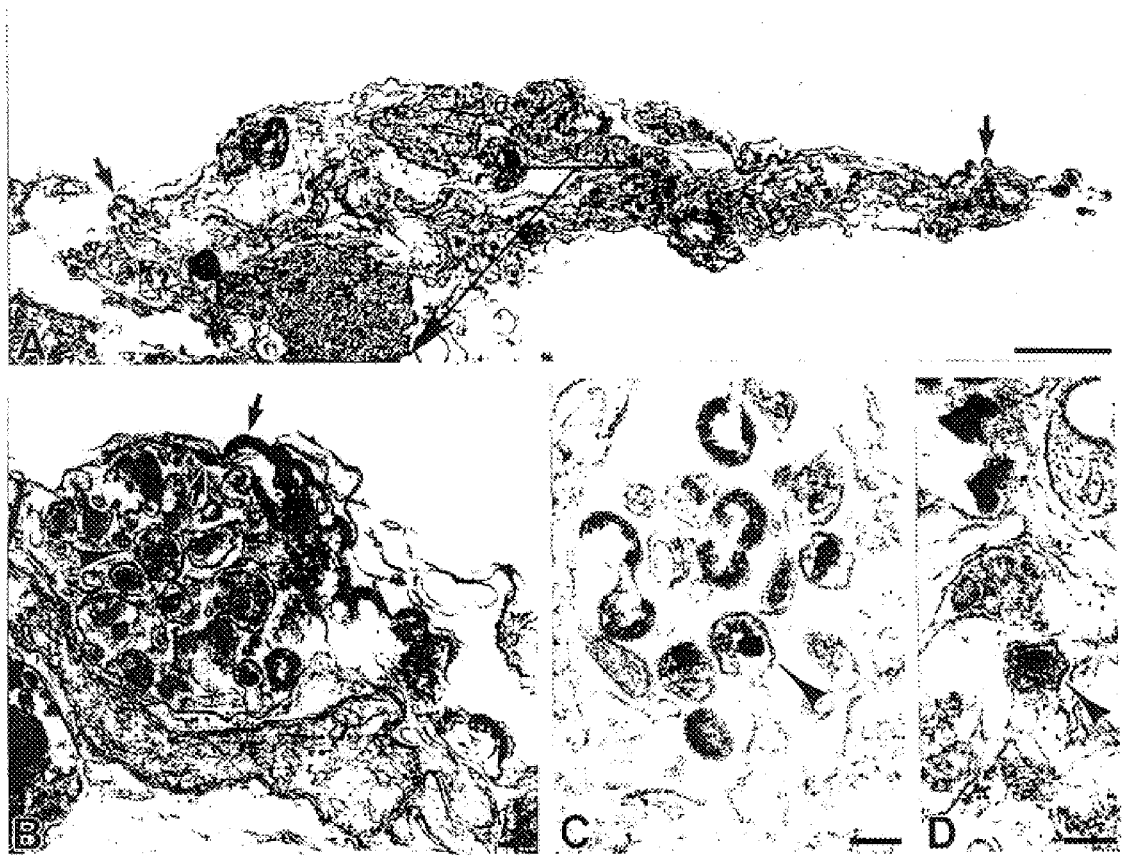
FIG. 9. Electron micrographs of cells transfected with NLVpr-H-PC1 constructs. A) Low power magnification showing an abundance of viral buds (arrows) at the cell membrane. Bar, lum. B) Enlarged area of (A) showing whole viral particles (Arrowheads) within a membrane-bound vacuole. Note the viral buds (arrows). Bar, 100 nm. C,D) Mature viral particles attached to the cell membranes (arrowheads). Bars, 100 nm.

As viral particles go through an ordered processing of precursor proteins to attain their characteristic morphology, it was of interest to examine the structure and maturation of viral particles produced by the chimeric Vpr-containing proviral DNA. One would expect a correlation between lack of infectivity and aberrant virus morphology. While virus particles with typical lentivirus morphology were observed in cell cultures transfected with both wild-type and chimeric proviral DNA, the number of typical particles was considerably less in the case of the latter. Moreover, cells transfected with chimeric proviral DNA showed an abnormal accumulation of viral buds and ring-shaped particles (FIG. 9A). Some of these cells had mature particles within membrane-bound vacuoles (FIG. 9B). Also of interest was the unusual presence of viral particles containing a mature core still attached to the cell membrane in the cells transfected with NLVpr-PC1 and NLVpr-H-PC1 (FIGS. 9C, D).

Discussion

The studies presented here outline an unique strategy to contain HIV-1 replication based on the colocalization of the antiviral agent with the target protein in the virus particles. The processing of the viral precursor proteins, mediated by HIV-1 PR, has been shown to take place in two different compartments (Hunter,1994; Kohl et al., 1988). The intracellular processing of viral proteins by PR is likely to exclude the processed proteins from associating with the budding virus particles. The processing of proteins that occurs in the virus particles converts the immature into mature infectious particles (Katz and Skalka,1994; Kohl et al., 1988). Since the latter process is carried out in an isolated compartment away from host cells, the concept of virion-specific therapeutic molecules is appealing as an approach to disrupt virus replication. The generation of an infectious virus particle is strictly dependent upon the completion of processing by the viral PR (Katz and Skalka, 1994; Debouck, 1992; Katoh et al., 1989; Kaplan et al., 1993). Therefore, the crucial role and the specificity of PR for viral proteins have generated intense efforts to identify effective inhibitors targeting the enzyme to prevent virus maturation.

The virion-specific therapeutic molecule generated from within provides high specificity for its incorporation into the virus particles. Among the three auxiliary gene products that are incorporated into HIV-1 viral particles, Vif, Vpr and Nef (Trono, 1995; Subbramanian et al., 1994; Welker et al., 1996; Pandori et al., 1996; Natsoulis et al., 1991), the Vpr molecule, due to its small size, abundance, and stability, best meets the criteria for a vehicle to deliver a peptide of interest into the virus particle. Since Vpr does not influence virus morphogenesis, this approach is more advantageous than the capsid fusion approach, where the exogenous sequences targeting the virus are fused to the capsid (Natsoulis et al., 1995; Wills and Craven, 1991; Kaplan et al., 1994).

The extent of incorporation of viral proteins such as Gag, Gag-Pol and chimeric Vpr further lends credence to the strategy outlined here. It is reported that each virus particle contains 2500 copies of Gag and approximately 1/10 or 1/20 of Gag-Pol polyproteins (Hunter et al., 1994; Wills, 1991). Though the exact number is not available for HIV-1 Vpr, it is present in high amounts, as the Vpr-related Vpx has been shown to be present in equimolar concentration as that of p24 of HIV-2 Gag (Henderson et al., 1988). Such a scenario presents a situation in which the concentration of Vpr-PC1 and Vpr-H-PC1 proteins is in excess of that of Gag-Pol, and may lead to a reduction in the level of active PR available.

Viral populations derived from the HIV-1 proviral DNA containing chimeric Vpr showed lower replication in comparison to wild type HIV-1 proviral DNA. Further, the extent of replication was lower with chimeric Vpr containing a flexible hinge region between Vpr and PR coding sequences (Vpr-H-PC1). The addition of hinge region residues (G-G-S-S-G, Gly-Gly-Ser-Ser-Gly) may provide flexibility to the dimer interface domain so that the chimeric Vpr molecules are able to form stable structures with PR monomers. This results in inactive PR, and leads to the generation of non-infectious virus particles. This is indeed supported by the data from both multiple and single round replication assays.

The mechanisms by which Vpr-PC1 and Vpr-H-PC1 bring about this effect on virus infectivity is not clear. The reduced availability of active PR and interference with virion maturation events through incomplete processing of precursor viral proteins may account for the inhibitory effects observed. Analysis of viral proteins in cells and in virus particles may provide clues as to the mechanism involved in reduced virus infectivity.

Ultrastructural studies revealed abnormalities at the budding stage and at the time of particle release. These data are in agreement with the observation showing a link between the level of PR activity and virion release (Kaplan et al., 1994). Zhang et al. (1991), have shown that a peptide corresponding to the C-terminus of PR inhibited PR activity in vitro. Similarly, Bab6 et al. (1992), noted that a 13 amino acid peptide representing N- and C-termini of PR inhibited PR activity and prevented the assembly of PR dimers in refolding experiments in vitro. In contrast to the data reported here, only a weak effect was noted with respect to virus replication in MT4 cells using a peptide from the dimer interface structure (Schramm et al., 1991). This may be due to the inefficient localization of the peptide in the virus particle. It is likely that the presentation of a dimer interface domain in the context of a protein with specificity for incorporation into virus particles may bring the domain close to the target precursor Gag-Pol protein containing PR. The novel agents described here may provide useful information for the development of peptide mimetics to contain HIV-1 replication. Interestingly, Vpr-PC1 and Vpr-H-PC1 lack the cell cycle arrest function which enables the use of modified Vpr as an effective and specific delivery vehicle for genetic approaches to treat HIV-1 infection.

TABLE 3

Effect of Vpr-C on Virus Replication

| | RT activity in culture supernatant, cpm/ul | | | | |
|---|---|---|---|---|---|
| Virus Derived from Designated proviral DNA | 5 days after infection | 9 days after infection | 16 days after infection | 20 days after infection | 26 days after infection |
| *NL4-3 | 42 | 3999 | 7513 | 10764 | 2184 |
| NLVpr-PC1 | 0 | 0 | 4127 | 5504 | 3888 |
| NLVpr-H-PC1 | 0 | 0 | 758 | 5162 | 4611 |

*The replication pattern of virus derived from NLVpr-F and NLVpr-PKA was similar to NL4-3

TABLE 4

Effect of Vpr-C on Virus infectivity in a single round of replication

| Proviral VPR clones | Titers CFU/ml* | % (+) Inhibition† |
|---|---|---|
| ED84†† | 1760 | 0 |
| NLVpr-PC1 HYG | 590 | 66 |
| NLVpr-H-PC1 HYG | 352 | 80 |

*NO Hygr colonies were observed for any of the proviral clones when the trans-complementation was performed without pSDV-A-MLV-env, pSV-A-ML-env by itself, or mock transfected.
†Extent of inhibition was calculated in comparison to ED84 control proviral DNA.
††The virus derived from NLVpr-F and NLVpr-PKA proviral DNA showed replication results similar to virus from ED84 control.

REFERENCES IDENTIFIED BY NUMBER

1. Levy, J. A. (1993) *Microbiol. Rev.* 57, 183–289.

2. Debouck, C. (1992) *AIDS Res. Hum. Retroviruses* 8, 153–164

3. Ridky, T. & Leis, J. (1995) *J. Biol. Chem.* 270, 29621–29623.

4. Miller, R. H., Turk, S. R., Black, R. J., Bridges, S. & Sarver, N. (1996) *AIDS Res. Hum. Retrovirises* 12, 859–864.

5. Mellors, J. M. (1996) *Nat. Med.* 2, 274–295.

6. Villa, S. (1995) *J. Acquired Immune Defic.Syndr. Hum. Retroviral* 10, Suppl. 1, S58–S61.

7. Crowe, S., Cooper, D. A. & Chambers, D. E. (1996) *MJA.* 164, 290–295.

8. Collier, A. C., Coombs, R. W., Schoenfied, D. A., Bassett, R. L., Timpoone, J., Baruch, A., Jones, M., Facey, K., Whitacre, C., McAuliffe, V. J., Friedman, H. M., Merigan, T. C., Reichman, R. C., Hooper, C. & Corey, L. (1996) *New Engl. J. Med,* 334, 1011–1017.

9. Larder, B. A., Kohli, A., Bloor, S., Kemp, S. D., Harrigan, P. R., schooley, R. T., Lange, J. M. A., Pennington, K. N., St. Clair, M. H. & The Protocal 34,225–02 Collaborative Group (1998) *J. Virol.* 70. 5922–5929.

10. Jablonowski, H. (1995) *J. Acquired Immune Defic. Syndr. Hum. Retroviral.* 10, Suppl. 1, S28–S33.

11. Larder, B. A. (1995) *J. Acquired Immune Defic. Syndr. Hum. Retroviral.* 10, Suppl. 1, S28–S33.

12. Cohen, E. A., Dehni, G. Sodroski, J. G. & Haseltine, W. A. (1990) *J. Virol.* 64, 3097–3099.

13. Liu, H., Wu, X., Newman, M. Shaw, G. M., Hahn, B. & Kappes, J. C. (1995) *J. Virol.* 699, 7630–7638.

14. Camzur, D. & Trono, D. (1996) *J. Virol.* 70, 6106–6111.

15. Welker, R., Kottler, H., Kalbitzer, H. R. & Kräusslich, H. -G. (1996) *Virology* 219, 228–236.

16. Pandori, M. W., Fitch, N. J. S., Craig, H. M., Richman, S. D., Spina, C. A. & Guatelli, J. C. (1996) *J. Virol.* 70, 4283–4290.

17. Myers, G., Korber, B., Wain-Hobson, S. & Smith, R. F. (1993) *Hum. Retroviruses and AIDS* (Los Alamos National Lab., Los Alamos, N. Mex.).

18. Lu, Y. L., Spearman, P. & Ratner, L. (1993) *J. Virol.* 67, 6542–6550.

19. Re, F., Braten, D., Frank, E. K. & Luban, J. (1995) *J. Virol.* 69, 6859–6864.

20. Jowett, J. B., Planelles, V., Poon,, B., Shah, N. P., Chen, M. & Chen I. S. (1995) *J. Virol.* 69, 6304–6313.

21. Rogel, M. E., Wu, L. I. & Emmerman, M. (1995) *J. Virol.* 69, 882–888.

22. He, J., Choe, S. Walker, R., DiMarzio, P., Morgan, D. O. & Landau, N. (1995) *J. Virol.* 69, 6705–6711.

23. Zhao, L. J., Wang, L. Mukherjee, S. & Narayan, O. (1994) *J. Biol. Chem.* 269, 32131–32137.

24. Lu, Y. L., Spearman, P. & Ratner, L. (19.) *J. Virol.* 67, 6542–6550.

25. Heinzinger, N. K., Bukrinsky, M. I., Haggerty, S. A., Ragland, A. M., Kewairamani, V., Lee, M. A., Gendelman, H. E., Ratner, L., Stevenson, M. & Emmerman, M. (1994) *Proc. Natl. Acad. Sci. USA* 91, 7311–7315.

26. Piller, S. C., Ewart, G. D. Premkumar, A. Cox, G. B. & Gage, P. W. (1996) *Proc. Natl. Acad. Sci. USA* 93, 111–115.

27. Bouhamdan, M. Benichou, S., Rey, F., Navarro, J. M., Agostini, I., Spore, B., Camonis, J., Slupphaug, G., Vigne, R., Benarous, R. & Sire, J. (1996) *J. Virol.* 70, 697–704.

28. Refaeli, Y., Levy, D. N. & Weiner, D. B. (1995) *Proc. Natl. Acad. Sci. USA* 92, 3621–3625.

29. Balliet, J. W., Kolson, D. L., Eiger, G., Kim, F. M., McGann, K. A., Srinivasan, A. & Collman R. (1994) *Virology* 200, 623–631.

30. Westervelt, P., Henkel, T., Trowbridge<D. B., Orenstein, J., Heuser, J. Gendelman, H. H. & Ratner, L. (1992) *J. Virol.* 68, 6161–6169.

31. Mahalingam, S., Khan, S. A., Murali, R., Jabbar, M. A. Monken, C. E., Collman, R. G. & Srinivasan, A. (1995) *Proc. Natl. Acad. Sci. USA* 92, 3794–3798.

32. Mahalingam, S., Khanm S. A., Jabbar, M. A., Monken, C. E., Collman, R. G. & Srinivasan, A. (1995) *Virology* 207, 297–302.

33. Mahalingam, S., Collman, R. G., Patel, M. Monken, C. E. & Srinivasan, A. (1995) *Virology* 210, 495–500.

34. Mahalingam, Collman, R. G., S., Patel, M., Monken, C. E. & Srinivasan, A. (1995) *Virology* 210, 331–339.

35. Mahalingam, Patel, M., Collman, R. G. & Srinivasan, A. (1995) *Virology* 214, 647–652.

36. Yao, X. J., Subbramanian, R. A., Rougeau, N., Boisvert, F. Bergeron, D. & Cohen, E. A. (1995) *J. Virol.* 69, 7032–7044.

37. Paxton, W., Connor, R. I. & Landau, N. (1993) *J. Virol.* 67, 7229–7237.

38. Di Marizo, P., Choe, S., Ebright, M., Knoblauch, R. & Landau, N. *J. Virol.* 69, 7909–7916.

39. Hunter, E. (1994) Semin. *Virol.* 5, 71–83.

40. Nagashunmugam, T., Velpandi, A., Goldsmith, C. S., Zaki, S. R., Kalyanaraman, V. S. & Srinivasan, A. (1992) *Proc. Natl. Acad. Sci. USA* 89, 4114–4118.

41. Rizvi, T. A. & Panganiban, A. (1992) *AIDS Res. Hum. Retrovirus* 8, 89–95.

42. Rizvi, T. A., Schmidt, R. D., Lew, K & Keeling, M. E. (1996) *Virology* 222, 457–463.

43. Rizvi, T. A., Lew, K. A. Murphy, E. C. & Schmidt, R. D. (1996) *Virology* 224, 517–532.

44. Delwart, E. L., Buchschacher, G. L., Jr., Freed, E. O. & Panganiban, A. T. (1992) *AIDS Res. Hum. Retrovirus* 8, 1669–1677.

45. Page, K. A., Landau, N. R. & Littman, D. R. (1990) *J. Virol.* 64, 5270–5276.

46. Tözsér, J., Bláha, I., Copeland, T. D., Wondrak, E. M. & Oroszian, S. (1991) *FEBS Lett.* 281, 77–80.

47. Darke, P. L., Nutt, R. F., Brady, S. F., Garsky, V. M., Ciccarone, T. M., Leu, C., Lumma, P. K., Freidinger, R. M., Veber, D. F. & Sigal, I. S. (1988) *Biochem. Biophys. Res. Commun.* 156, 297–303.

48. Billich, S., Knoop, M. T., Hansen, J., Strop, P., Sedlacek, J., Mertz, R. & Moelling, K. (1988) *J. Biol. Chem.* 263, 17905–17908.

49. Moore, M. L., Btyan, W. M., Fakhoury, S. A., Magaard, V. W., Huffman, W. F., Dayton, B. D., Meek, T. D., Hyland, L. Dreyer, G. B., Metcalf, B. W., Strickler, J. E., Gorniak, J. G. & Debouck, C. (1989) *Biochem. Biophys. Res. Commun.* 159, 420–425.

50. Tritch, R. J. M., Cheng, Y. S., Yin, F. H. & Erickson-Viitanen, S. (1991) *J. Virol.* 65, 922–930.

51. Katz, R. A. & Skalka, A. M. (1994) *Annu. Rev. Biochem.* 63, 133–73.

52. Natsoulis, G. & Boeke, J. D. (1991) *Nature* (London) 352, 632–635.

53. Pasten, I., Chaudary, V. & Fitzgerald, (1992) *Annu. Rev. Biochem.* 61, 331–354.

54. Trono, D. Feinberg, M. B. & Baltimore, D. (1989) *Cell*, 59, 113–120.

55. Malim, M. H., Freimuthm W. W., Liu, J., Boyle, T. J., Lyerly, H. K., Cullen, B. R. & Nabel, G. J. (1992) *J. Exp. Med.* 76, 1197–1201.

56. Pearson, L., Garcia, J., Wu, F., Modesti, N., Nelson, J. & Gaynor, R. (1990) *Proc. Natl. Acad. Sci. USA* 85, 5079–5083.

57. Freed, E. O., Delwart, E. L., Buchschacher, G. L., Jr., & Panganiban, A. T. (1992) *Proc. Natl. Acad. Sci. USA* 89, 70–74

58. Wu, X., Liu, H., Xiao, H., Kim, J., Seshaiah, S., Natsoulis, G., Boeke, J. D., Hahn, B. H. & Kappes, J. C. (1995) *J. Virol.* 69, 3389–3398.

59. Wu, X., Liu, H., Xiao, Conway, J. A. & kappes, J. C. (1996) *J. Virol.* 70, 3378–3384.

60. Cameron, C. E., Grinde, B., Jentoft, J., Leis, J., Weber, I. T., Copeland, T. D. & Wlodawer, A., (1992) *J. Biol. Chem.* 267, 23735–23741.

61. Pettit, S. C., Moody, M. D., Wehbie, R. S., Kaplan, A. H., Nantermet, P. V., Klein, C. A. & Swanstrom, R. (1994) *J. Virol.* 68, 8017–8027.

62. Henderson, L. E., Sowder, T. D., Copeland, R. E., eneveniste, R. E. & Oroszlan, S. (1988) *Science* 241, 199–201.

63. LeGrice, S. F. J., Ette, R., Mills, J. & Mous, J. (1989) *J. Biol. Chem.* 264, 14902–149008.

64. Partin, K., Zybarth, G., Ehrlich, L., DeCrombrugghe, M., Wimmer, E. & Carter, C., (1991) *Proc. Natl. Acad. Sci. USA* 88, 4776–4780.

65. Sheng, N. & Erickson-Viitanen, S. (1994) *J. Virol.* 68, 6207–6214.

66. Rosé, J. R., Babé, ilia, M. & Craik, C. S. (1995) *J. Virol.* 69, 2751–2758.

REFERENCES IDENTIFIED BY AUTHOR AND YEAR

Adachi, A., Gendelman, H. E., Koenig, S., Folks, T., Willey, R., Rabson, A. & Martin, M. A. (1986). Production of acquired immunodeficiency—associated retrovirus in human and non human cells transfected with an infectious molecular clone. *J. Virol.* 59, 284–291.

Babé, L. M., Pichuantes, S. & Craik, C. S. (1991). Inhibition of HIV protease activity by heterodimer formation. *Biochemistry* 30, 106–111.

Babé, L. M., Rose, J. & Craik, C. S. (1992). Synthetic "interface" peptides alter dimeric assembly of the HIV-1 and 2 proteases *Protein Science* 1, 1244–1253.

Babé, L. M., Rose, J. & Craik, C. S. (1995). Trans-dominant inhibitor of human immunodeficiency virus type 1 protease monomers prevent protease activation and virion maturation. *Proc. Natl. Acad. Sci. USA* 92, 10069–10073.

Cohen, E. A., Gaudreau, P., Brazeau, P. & Langelier, Y. (1986). Specific inhibition of herpesvirus ribonucleotide reductase by a nonapeptide derived from the carboxy terminus of subunit 2. *Nature* (London) 321, 441–443.

Collier, A. C., Coombs, R. W., Schoenfield, D. A., Bassett, R. L., Timpoone, J., Baruch, A., Jones, M., Facey, K., Whitacre, C., McAuliffe, V. J., Friedman, H. M., Merigan, T. C., Reichman, R. C., Hooper, C., & Corey, L. (1996). Treatment of human immunodeficiency virus infection with saquinavir, zidovudine and zalcitabine. *New. Eng. J. Med.* 334, 1011–1017.

Divita, G., Restle, T., Goody, R. S., Chermann, J. C. and Baillon, J. G. (1994). Inhibition of human immunodeficiency type-1 reverse transcriptase dimerization using synthetic peptides derived from the connection domain. *J. Biol. Chem.* 269, 13080–13083.

Dutia, B. M., Frame, M. C., Subak-Sharpe, J. H., Clark, W. N. & Marsden, H. S. (1986). Specific inhibition of herpesvirus ribonucleotide reductase by synthetic peptides. *Nature* (London) 321, 439–441.

Embretson, J., Lupancic, M., Ribas, J. L., Burke, A., Racz, P., Tenner, K. & Haase, A. T. (1993). Massive covert infection of helper T lymphocytes and macrophages by HIV during the incubation period of AIDS. *Nature* (London) 362, 359–362.

Emerman, M. (1996). HIV-1, Vpr and the cell cycle. *Curr. Biol.* 6, 1096–1103.

Freed, E. O., Delwart, E. L., Buchschacer, G. L. Jr. & Panganiban, A. T. (1992). A mutation in the human immunodeficiency virus type 1 transmembrane glycoprotein gp41 dominantly interferes with fusion and infectivity. *Proc. Natl. Acad. Sci. USA* 89, 70–74.

Henderson, L. E., Sowder, T. D., Copeland, R. E., Beneveniste, R. E. & Oroszlan, S. (1988). Isolation and characterization of a novel protein (X-ORF product) from SIV and HIV-2. *Science* 241, 199–201.

Hunter, E. (1994). Macromolecular interactions in the assembly of HIV and other retroviruses *Sem. in Virol.* 5, 71–83.

Jablonowski, H. (1995). Studies of zidovudine in combination with didanosine and zalcitabine. *J.Acquir.Immune Defic. Synd. Hum. Retrovirol.* 10(Suppl.1), S52–S56.

Kaplan, A. H. & Swanstrom, R. (1991). Human immunodeficiency virus type1 Gag proteins are processed in two cellular compartments. *Proc. Natl. Acad. Sci. USA* 88, 4528–4532.

Kaplan, A. H., Zack, J. A., Knigge, M., Paul, D. A., Kempf, D. J., Norbeck, D. W. & Swanstrom, R. (1993). Partial inhibition of the human immunodeficiency virus type-1 protease results in aberrant virus assembly and the formation of non-infectious particles. *J. Virol.* 67, 4050–4055.

Kaplan, A. H., Manchester, M. & Swanstrom, R. (1994). The activity of the protease of human immunodeficiency type-1 is initiated at the membrane of infected cells before the release of viral proteins and is required for release to occur with maximum efficiency. *J. Virol.* 68, 6782–6786.

Katoh, I., Ikawa, Y. & Yoshinaka, Y. (1989). Retrovirus protease characterized as a dimeric aspartic proteinase. *J. Virol.* 63, 2226–2232.

Katz, R. A. and Skalka, A. M. (1994). The retroviral enzymes. *Annu. Rev. Biochem.* 63, 133–173.

Kimpton, J., and Emerman, M. (1992). Detection of replication-competent and pseudotyped human immunodeficiency virus with a sensitive cell line on the basis of activation of an integrated fg-galactosidase gene. *J.Virol.* 66, 22322239.

Kohl, N. E., Emini, E. A., Schleif, W. A., Davis, L. J., Heimbach, J. C., Dixon, R. A., Scolnick, E. M. & Sigal, I. S. (1988). Active human immunodeficiency virus protease is required for viral infectivity. *Proc. Natl. Acad. Sci. USA* 85, 46864690.

Larder, B. A. (1995). Viral resistance and the selection of anti-retroviral combinations. *I. Acquir. Immune Defic. Synd. Hum. Retrovirol.* 10 (Suppl.1), S28–S33.

Larder, B. A., Kohli, A., Bloor, S., Kemp, S. D., Harrigan, P. R., Schooley, R. T., Lange, J. M. A., Pennington, K. N., St.Clair, M. H. & the Protocol 34,225-02 Collaborative Group. (1996). Human immunodeficiency virus type 1 drug susceptibility during zidovudine (AZT) monotherapy compared with AZT and 2',3' dideoxyinosine or AZT and 2',3' dideoxyinosine combination therapy. *J. Virol.* 70, 5922–5929.

LaVallee, C., Yao, X. J., Ladha, A., Gottlinger, H., Haseltine, W. A. & Cohen, E. A. (1994). Requirement of the Pr55gag precursor for incorporation of the Vpr product into human immunodeficiency virus type I viral particles. *J. Virol.* 68, 1926–1934.

Levy, J. A. (1993). Pathogenesis of human immunodeficiency virus infection. *Microbiol.Rev.* 57, 183–289.

Lu, Y. L., Spearman, P. & Ratner, L. (1993). Human immunodeficiency virus type 1 viral protein R localization in infected cells and virions. *J. Virol.* 67, 6542–6550.

Mahalingam, S., Khan, S. A., Murali, R., jabbar, M. A., Monken, C. E., Collman, R. G. & Srinivasan, A. (1995a). Mutagenesis of the putative alpha-helix domain of the Vpr protein of human immunodeficiency virus type-1: effect on stability and virion incorporation. *Proc. Natl. Acad. Sci. USA* 92, 3794–3798.

Mahalingam, S., Khan, S. A., jabbar, M. A., Monken, C. E., Collman, R. G. & Srinivasan, A. (1995b). Identification of residues in the N-terminal acidic domain of HIV-1 Vpr essential for virion incorporation. *Virology* 207, 297302.

Mahalingam, S., Collman, R. G, Patel, M., Monken, C. E. & Srinivasan, A. (1995c). Role of the conserved dipeptide Gly75 and Cys76 on HIV-1 Vpr function. *Virology* 210, 495–500.

Mahalingam, S., Collman, R. G, Patel, M., Monken, C. E. & Srinivasan, A. (1995d). Functional analysis of HIV-1 Vpr: identification of determinants essential for subcellular localization. *Virology* 212, 331–339.

Mahalingam, S., Patel, M., Collman, R. G, & Srinivasan, A. (1995e). The carboxy-terminal domain is essential for stability and not for virion incorporation of HIV-1 Vpr into virus particles. *Virology* 214, 647–652.

Malim, M. H., Freimuth, W. W., Liu, J., Boyle, T. J., Lyerly, H. K., Cullen, B. R. & Nabel, G. J. (1992). Stable expression of transdominant Rev protein in human T cells inhibits human immunodeficiency virus replication. *J. Exp. Med.* 76, 1197–1201.

Mellors, J. M. (1996). Closing in on human immunodeficiency virus type 1. *Nature Med.* 2, 274–295.

Miller, R. H., Turk, S. R., Black, R. J., Bridges, S. & Sarver, N. (1996). Conference Summary: Novel HIV Therapies—from discovery to clinical proof of concept. *AIDS Res. Human Retroviruses.* 12, 859–864.

Myers, G., Korber, B., Wain-Hobson, S. & Smith, R. F. (1993) *Htiman Retroviruses and AIDS.* Los Alamos Natl.Lab., Los Alamos, N. Mex.

Nagashunmugam, T., Velpandi, A., Goldsmith, C. S., Zaki, S. R., Kalyanaraman, V. S., & Srinivasan, A. (1992). Mutation of the primer binding site of the type I human immunodeficiency syndrome genome affects virus production and infectivity. *Proc. Natl. Acad. Sci. USA* 89, 41144118.

Natsoulis, G., Boeke, J. D. (1991). New antiviral strategy using capsid-nuclease fusion proteins. *Nature* 352, 632–635.

Natsoulis, G., Seshaiah, P., Federspiel, M. J., Rein, A., Hughes, S. H. & Boeke, J. D. (1995). Targeting of nuclease to murine leukemia virus capsids inhibits viral multiplication. *Proc. Natl. Acad. Sci. USA* 92, 364–368.

Pandori, M. W., Fitch, N. J. S., Craig, H. M., Richman, D. D., Spina, C. A. & Guatelli, J. C. (1996). Producer-cell modification of human immunodeficiency virus type-1: Nef is a virion protein. *J. Virol.* 70, 4283–4290.

Pantaleo, G., Graziosi, C., Demarest, J. F., Butini, L., Montroni, M., Fox, C. F., Orenstein, J. M., Kotler, D. P.

& Fauci, A. S. (1993). HIV infection is active and progressive in lymphoid tissue during the clinically latent stage of disease. *Nature* (London) 362, 355–358.

Paxton, W., Connor, R. I. & Landau, N. (1993). Incorporation of Vpr into human immunodeficiency virus type I virions: requirement for the p6 region of gag and mutational analysis. *J. Virol.* 67, 7229–7237.

Pearson, L. Garcia, J., Wu, F., Modesti, N., Nelson, J. & Gaynor, R. (1990). Transdominant tat mutant that inhibits tat-induced gene expression from the human immunodeficiency virus long terminal repeat. *Proc. Natl. Acad. Sci. USA* 87, 5079–5083.

Ridky, T. & Leis, J. (1995). Development of drug resistance to HIV-1 protease inhibitors. *J. Biol. Chem.* 270, 29621–29623.

Rizvi, T. A., Lew, K. A., Murphy, E. C., & Schmidt, R. D. (1996). Role of Masonpfizer monkey virus (MPMV) constitutive transport element (CTE) in the propagation of MPMV vectors by genetic complementation using homologous/heterologous env genes. *Virology* 224, 517–532.

Schinazi, R. F., Larder, B. A. & Mellors, J. W. (1996). Mutations in retroviral genes associated with drug resistance. *Int. Antiviral News* 4, 95–107.

Schramm, H. J., Nakashima, H., Schramm, W., Wakayama, H. & Yamamoto, N. (1991). HIV-1 reproduction is inhibited by peptides derived form the Nand C- termini of HIV-1 protease. *Biochem. Biophys. Res. Commun.* 179, 847851.

Schramm, H. J., Billich, A., Jaeger, E., Ruckhagel, K. P., Arnold, G. & Schramm, W. (1993). The inhibition of HIV-1 protease by interface peptides. *Biochem. Biophys. Res. Commun.* 194, 595–600.

Serio, D., Rizvi T. A., Cartas, M., Kalyanaraman V. S., Weber, I. T., Koprowski, H. and Srinivasan, A. (1997). Development of a novel anti-HIV-1 agent from within: Effect of chimeric Vpr-containing protease cleavage site residues on virus replication. *Proc. Natl. Acad. Sci. USA* 94, 3346–3351.

Subbramanian, R. A. and Cohen, E. A. (1994). Molecular biology of the human immunodeficiency accessory proteins. *J. Virol.* 68, 6831–6835.

Trono, D., Feinberg, M. B. & Baltimore, D. (1989). HIV-1 Gag mutants can dominantly interfere with the replication of the wild-type virus. *Cell* 59, 113120.

Trono, D. (1995). HIV accessory proteins: leading roles for the supporting cast. *Cell* 82, 189–192.

Weber, I. T. (1990). Comparison of the crystal structures and intersubunit interactions of human Immunodeficiency and Rous sarcoma virus proteases. *J. Bio. Chem.* 265, 10492–10496.

Welker, R., Kottler, H., Kalbitzer, H. R. & Krdusslich, H. -G. (1996). Human immunodeficiency virus type-I Nef protein is incorporated into virus particles and is specifically cleaved by the viral protease. *Virology.* 219, 228236.

Wills, J. W. & Craven, R. C. (1991). Form, function, and use of retroviral gag proteins. *AIDS* 5, 639–654.

Wlodawer, A., Miller, M., Jaskolski, M., Satyanarayana, B. K., Baldwin, E., Weber, I. T., Selk, L. M., Clawson, L., Schneider, J. & Kent, S. B. H. (1989). Conserved folding in retroviral protease: crystal structure of a synthetic HIV-1 protease. *Science* 245, 616–621.

Zhang, Z. Y., Poorman, R. A., Maggiora, L. L., Heinrikson, R. L. & Kezdy, F. J. (1991). Dissociative inhibition of dimeric enzymes. Kinetic characterization of the inhibition of HIV-1 protease by its COOH-terminal tetrapeptide. *J. Biol. Chem.* 266, 15591–15594.

---

What is claimed is:

1. A chimeric viral protein comprising:
   1) a protein of a virus; and
   2) a polypeptide of said virus,
said polypeptide joined by a peptide linkage to said viral protein in said chimeric protein, said polypeptide not normally joined by said peptide linkage to said protein in said virus or in cells infected by said virus.

2. A chimeric viral protein of claim 1 comprising:
   1) a protein of a virus, said protein not comprising a site for cleavage by a proteolytic enzyme of said virus;

2) a polypeptide proteolytic cleavage site of said virus, said cleavage site being a site for cleavage by a proteolytic enzyme of said virus;

such that said protein is covalently linked by a peptide linkage to said polypeptide proteolytic cleavage site.

3. A chimeric viral protein of claim 2 wherein the virus is an animal virus or a human virus.

4. A chimeric viral protein of claim 3 wherein the virus is a human virus.

5. A chimeric viral protein of claim 4 wherein the virus is selected from the group consisting of: herpes simplex virus type I, herpes simplex virus type II, human cytomegalovirus, human herpes virus type, and human immunodeficiency virus (HIV).

6. A chimeric viral protein of claim 5 wherein the virus is human immunodeficiency virus (HIV).

7. A chimeric viral protein of claim 3 wherein the protein of the virus is not a capsid protein of the virus.

8. A chimeric viral protein of claim 6 wherein the viral protein is the vpr protein.

9. A chimeric viral protein of claim 6 wherein the polypeptide proteolytic cleavage site corresponds to an amino acid sequence found in the Gag or Gag-Pol precursor proteins of HIV.

10. A chimeric viral protein comprising:
1) a non-capsid protein of a virus, the non-capsid protein not comprising a polypeptide proteolytic cleavage site for cleavage by a proteolytic enzyme;
2) a polypeptide of the virus, the polypeptide joined by a peptide linkage to the viral protein in said chimeric protein, wherein the polypeptide is not normally joined by the peptide linkage to the non-capsid protein in said virus or in cells infected by the virus.

11. A chimeric viral protein of claim 10 wherein the polypeptide has the cleavage site for cleavage by the proteolytic enzyme.

12. A chimeric viral protein of claim 11 wherein the cleavage site being a site for cleavage by the proteolytic enzyme of the virus.

13. A chimeric viral protein of claim 12 wherein the virus is an animal virus or a human virus.

14. A chimeric viral protein of claim 13 wherein the virus is a human virus.

15. A chimeric viral protein of claim 14 wherein the virus is selected from the group consisting of: herpes simplex virus type I, herpes simplex virus type II, human cytomegalovirus, human herpes virus type, and human immunodeficiency virus (HIV).

16. A chimeric viral protein of claim 15 wherein the virus is human immunodeficiency virus (HIV).

17. A chimeric viral protein of claim 16 wherein the polypeptide proteolytic cleavage site corresponds to an amino acid sequence found in the Gag or Gag-Pol precursor proteins of HIV.

18. A chimeric viral protein of claim 10, wherein the non-capsid protein is the vpr protein.

* * * * *